(12) United States Patent
Root et al.

(10) Patent No.: US 12,311,062 B2
(45) Date of Patent: May 27, 2025

(54) EXPANDING FOAM-FABRIC ORTHOPEDIC LIMB STABILIZATION DEVICE

(71) Applicant: President and Fellows of Harvard College, Cambridge, MA (US)

(72) Inventors: Samuel Evan Root, Cambridge, MA (US); Jovanna Angelina Fazzini, Cambridge, MA (US); Vanessa Sanchez, Cambridge, MA (US); Daniel John Preston, Cambridge, MA (US); George M. Whitesides, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 359 days.

(21) Appl. No.: 17/770,452

(22) PCT Filed: Oct. 21, 2020

(86) PCT No.: PCT/US2020/056625
§ 371 (c)(1),
(2) Date: Apr. 20, 2022

(87) PCT Pub. No.: WO2021/081070
PCT Pub. Date: Apr. 29, 2021

(65) Prior Publication Data
US 2022/0387658 A1 Dec. 8, 2022

Related U.S. Application Data

(60) Provisional application No. 62/923,938, filed on Oct. 21, 2019.

(51) Int. Cl.
*A61L 15/14* (2006.01)
*A61F 5/058* (2006.01)
*A61L 15/12* (2006.01)

(52) U.S. Cl.
CPC .............. *A61L 15/14* (2013.01); *A61F 5/058* (2013.01); *A61L 15/12* (2013.01)

(58) Field of Classification Search
CPC ...... A61L 15/14; A61L 15/12; A61L 2400/06; A61F 5/058; A61F 5/05866;
(Continued)

(56) References Cited

U.S. PATENT DOCUMENTS

| 3,301,252 A | 1/1967 | Mahoney, Jr. |
| 3,881,473 A | 5/1975 | Corvi et al. |

(Continued)

FOREIGN PATENT DOCUMENTS

WO WO-2021/081070 A1 4/2021

OTHER PUBLICATIONS

Ayzenberg et al., "A Simple Technique to Prolong Molding Time during Application of a Fiberglass Cast: An in Vitro Study," Orthopedic Reviews, Mar. 29, 2018, vol. 10:7314, pp. 8-10.
(Continued)

*Primary Examiner* — Ophelia A Hawthorne
(74) *Attorney, Agent, or Firm* — Wilmer Cutler Pickering Hale and Dorr LLP

(57) ABSTRACT

In one aspect, a kit includes a sleeve including an outer lining and an inner lining; a pouch arranged within the sleeve and including one or more polymer sheets, a plurality of channels, and a plurality of vents; and a foam precursor capable of forming a foam within the pouch. In one aspect, a method of stabilizing a body part includes providing a sleeve including an outer lining and an inner lining around a body part; providing a pouch arranged within the sleeve and including one or more polymer sheets, a plurality of channels, and a plurality of vents; providing a foam precursor in the pouch; and forming a foam within the pouch.

19 Claims, 20 Drawing Sheets

(58) Field of Classification Search
CPC .... A61F 5/05875; A61F 5/05858; A61F 5/01; A61F 5/04; A61F 13/00; A61F 13/04; C08L 63/00; C08L 75/04

See application file for complete search history.

(56) References Cited

U.S. PATENT DOCUMENTS

| | | | |
|---|---|---|---|
| 4,309,990 | A | 1/1982 | Brooks et al. |
| 4,483,332 | A | 11/1984 | Rind |
| 4,685,453 | A | 8/1987 | Guidnard et al. |
| 4,852,557 | A * | 8/1989 | Grim .................. A61F 5/05841 602/8 |
| 5,024,765 | A * | 6/1991 | Linder ............... B01D 67/0093 210/651 |
| 5,123,985 | A | 6/1992 | Evans et al. |
| 5,171,208 | A | 12/1992 | Edenbaum et al. |
| 5,390,682 | A | 2/1995 | Iams |
| 5,620,095 | A | 4/1997 | Delmore et al. |
| 6,695,801 | B1 | 2/2004 | Toronto et al. |
| 8,303,527 | B2 | 11/2012 | Joseph |
| 8,991,400 | B2 | 3/2015 | Lloyd |
| 2002/0133107 | A1 | 9/2002 | Darcey |
| 2004/0002671 | A1 | 1/2004 | Reaux |
| 2005/0033207 | A1 | 2/2005 | Anders |
| 2006/0155226 | A1 | 7/2006 | Grim et al. |
| 2011/0288518 | A1 * | 11/2011 | Roe .................. A61F 13/49004 604/391 |
| 2013/0053802 | A1 * | 2/2013 | Maidl ..................... A61F 5/445 604/332 |
| 2013/0324897 | A1 | 12/2013 | Martin |
| 2013/0331802 | A1 | 12/2013 | Collinge et al. |
| 2016/0262945 | A1 | 9/2016 | Han |
| 2017/0105863 | A1 | 4/2017 | Anderson et al. |
| 2017/0209293 | A1 | 7/2017 | Combs |
| 2017/0216078 | A1 | 8/2017 | Rivlin et al. |
| 2018/0153745 | A1 | 6/2018 | Troutner et al. |
| 2019/0328570 | A1 | 10/2019 | Tomblin et al. |

OTHER PUBLICATIONS

Blaya et al., "Design of an Orthopedic Product by Using Additive Manufacturing Technology: The Arm Splint," Journal of Medical Systems, Feb. 5, 2018, vol. 42(3):54. 4 pages.

Brubacher et al., "A Novel Cast Removal Training Simulation to Improve Patient Safety," Journal of Surgical Education, Jan.-Feb. 2016, vol. 73(1), pp. 7-11.

Buonamici et al., "A CAD-Based Procedure for Designing 3D Printable Arm-Wrist-Hand Cast," Computer-Aided Design and Applications (2019), 16(1), pp. 25-34.

Conn et al., "Sports and recreation related injury episodes in the US population, 1997-99," Injury Prevention, Jun. 1, 2003, vol. 9(2), pp. 117-123.

Davids et al., "Skin Surface Pressure Beneath an Above-the-Knee Cast: Plaster Casts Compared with Fiberglass Casts," The Journal of Bone and Joint Surgery, Apr. 1997, vol. 79-A, No. 4, pp. 565-569.

Guillen et al., "A Prospective Randomized Crossover Study on the Comparison of Cotton versus Waterproof Cast Liners," Hand, Mar. 2016, vol. 11(1), pp. 50-53.

Halanski et al., "Thermal Injury with Contemporary Cast—Application Techniques and Methods to Circumvent Morbidity," The Journal of Bone and Joint Surgery, Nov. 2007, vol. 89-A, No. 11, pp. 2369-2377.

International Search Report and Written Opinion mailed Feb. 2, 2021, in the International Application No. PCT/US2020/056625. 19 pages.

Kowalski et al., "Evaluation of Fiberglass versus Plaster of Paris for Immobilization of Fractures of the Arm and Leg," Military Medicine, Aug. 2002, vol. 167(8), pp. 657-661.

Marshall et al., "When Should a Synthetic Casting Material Be Used in Preference to Plaster-of-Paris? A Cost Analysis and Guidance for Casting Departments," Injury (1992), vol. 23(8), pp. 542-544.

Naranje et al., "Epidemiology of Pediatric Fractures Presenting to Emergency Departments in the United States," Journal of Pediatric Orthopaedics, Jun. 2016, vol. 36(4), e45-e48.

Shannon et al., "Waterproof Casts for Immobilization of Children's Fractures and Sprains," Journal of Pediatric Orthopaedics, Dec. 7, 2005, vol. 25(1), pp. 56-59.

Shore et al., "Epidemiology and Prevention of Cast Saw Injuries," The Journal of Bone and Joint Surgery, The Orthopaedic Forum, Feb. 19, 2014, vol. 96-A, No. 4, pp. e31: 1-8.

* cited by examiner

FIG. 2D
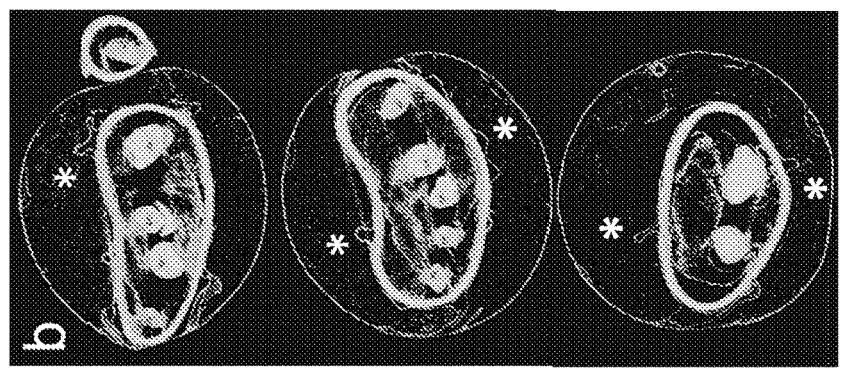
FIG. 2C
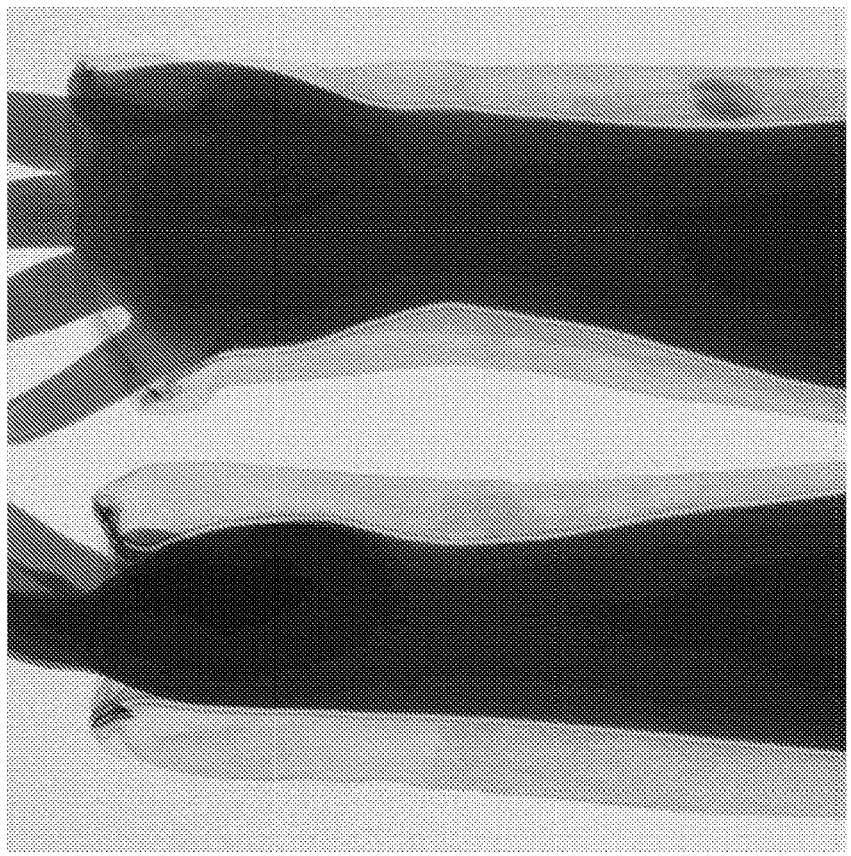
FIG. 2B
FIG. 2A

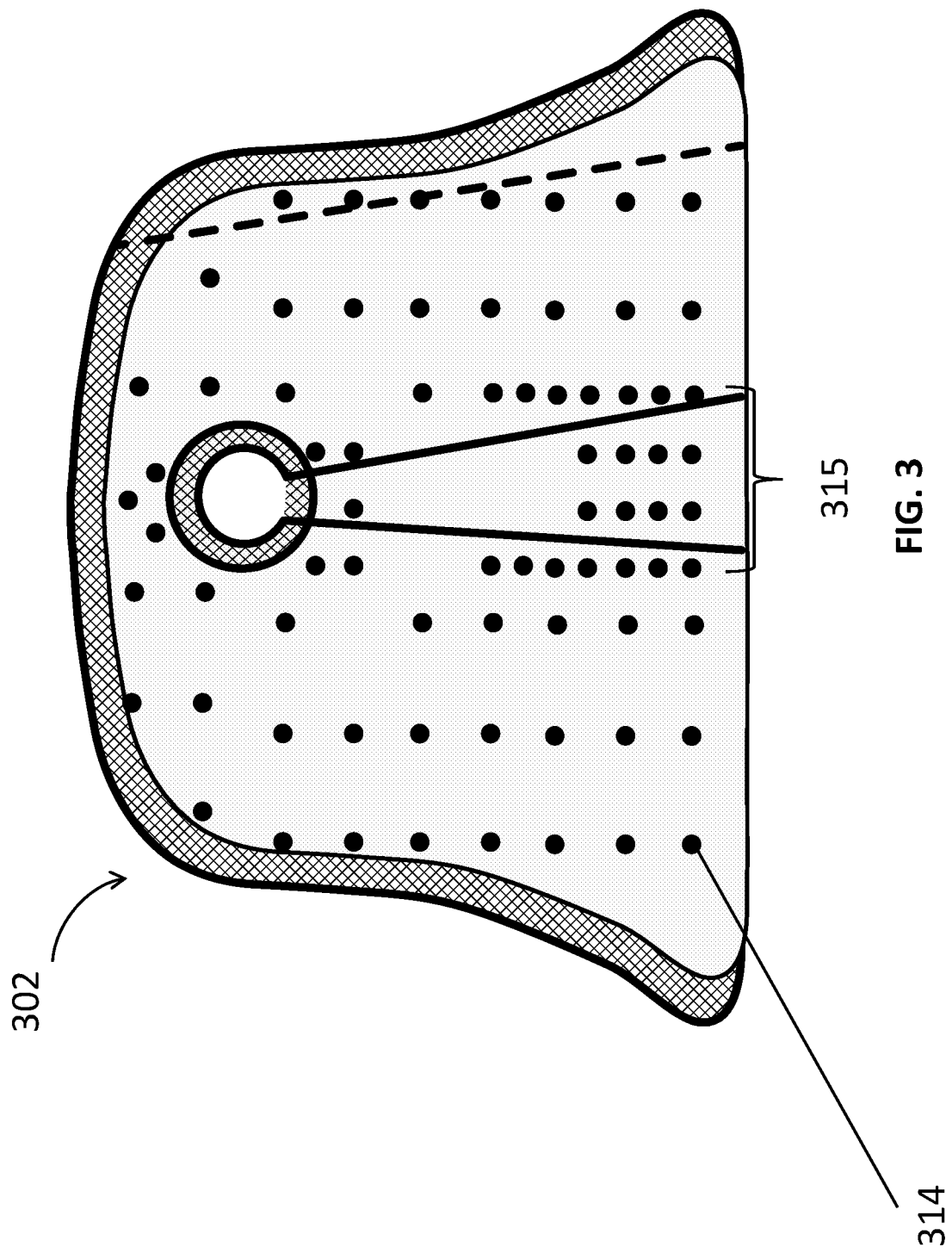

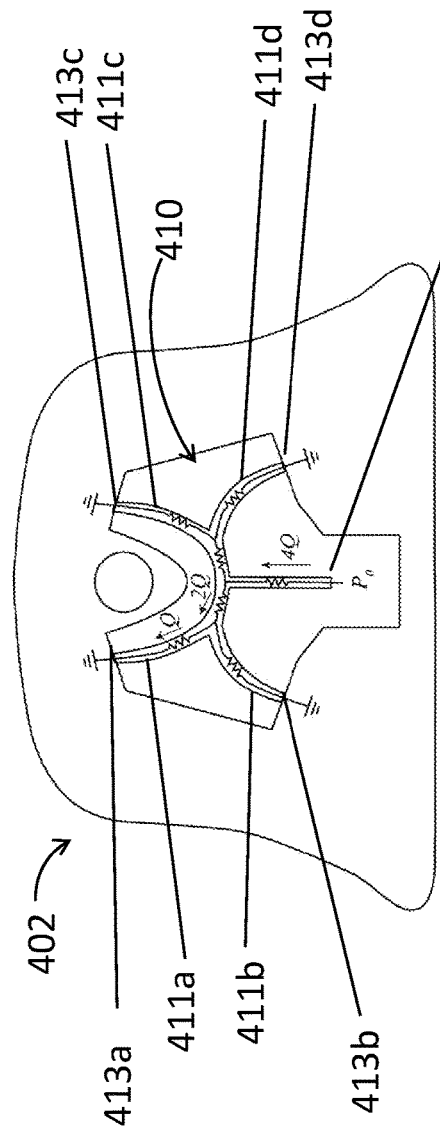
FIG. 4A
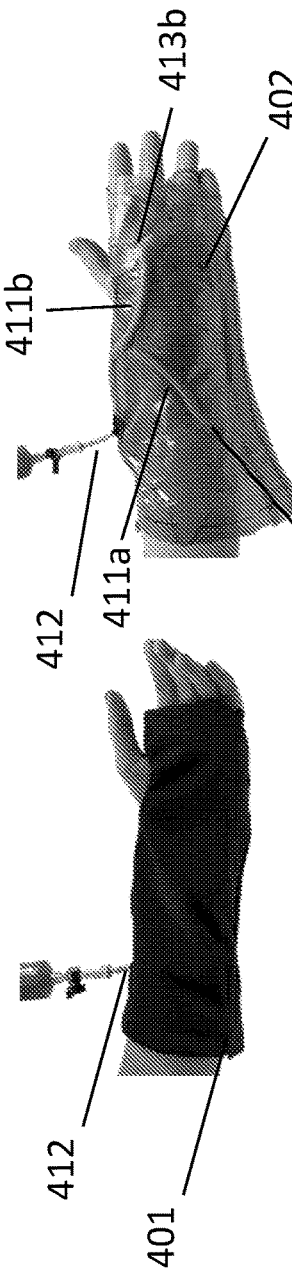
FIG. 4B
FIG. 4C
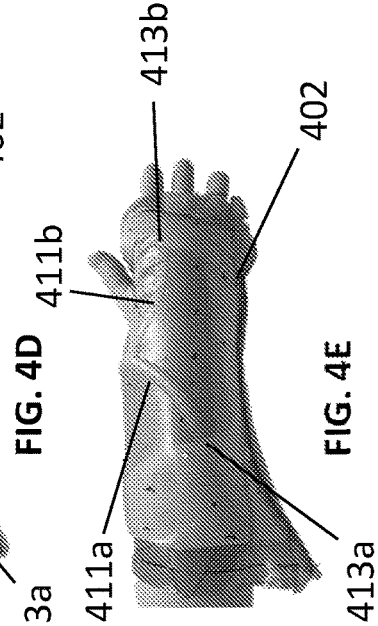
FIG. 4D
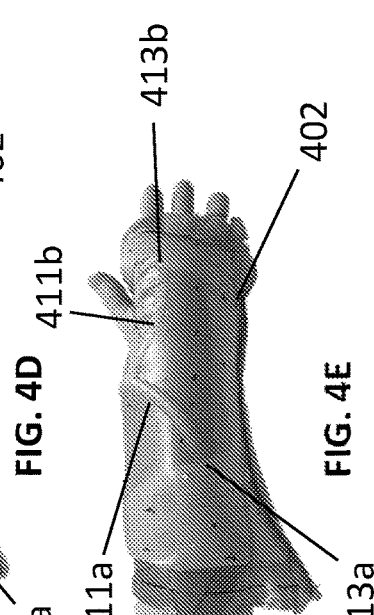
FIG. 4E

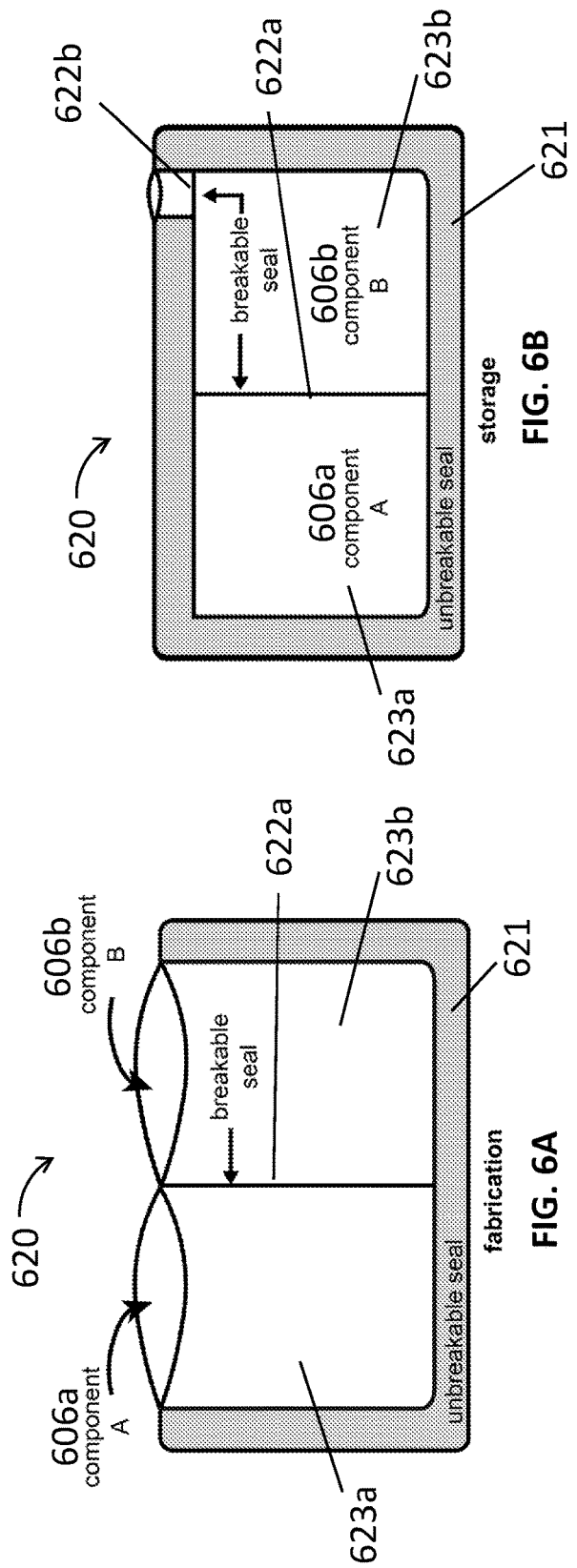
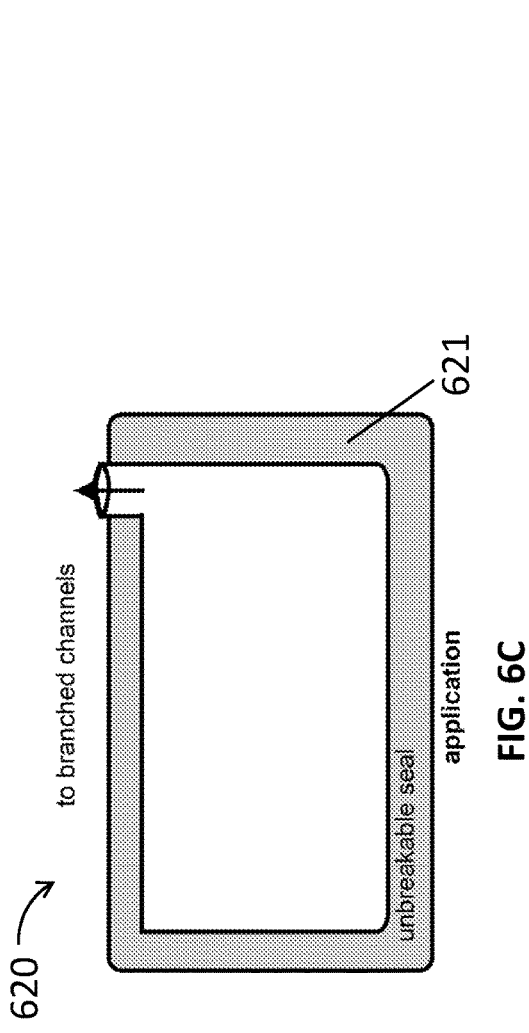
FIG. 6A
FIG. 6B
FIG. 6C

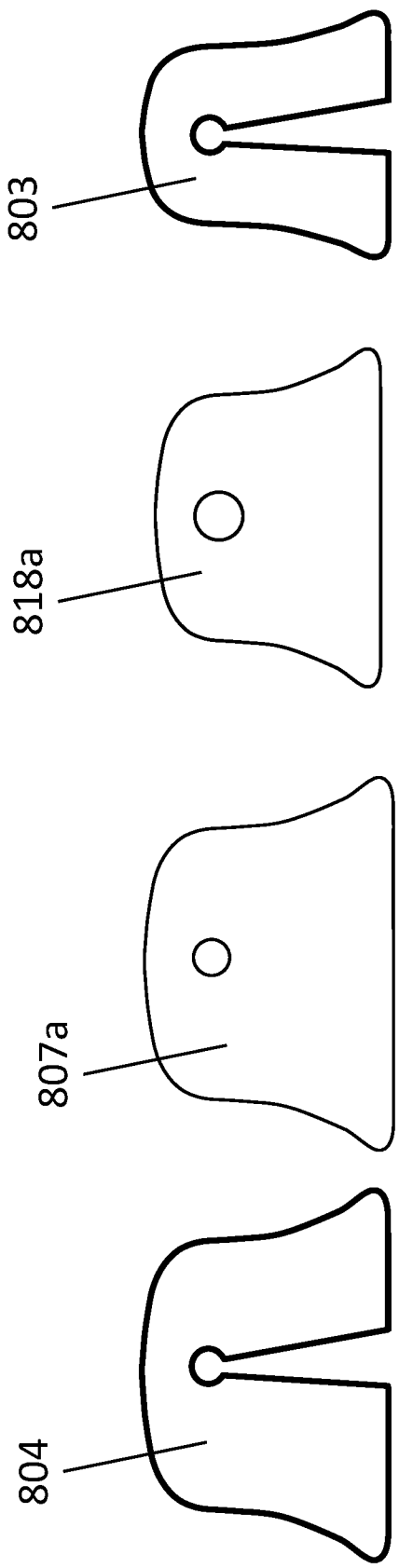
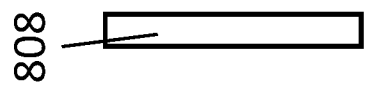
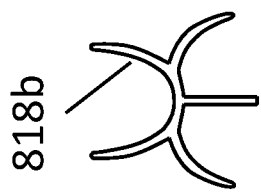
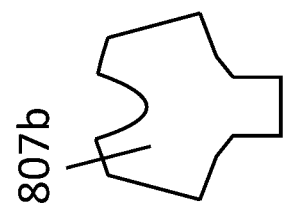
FIG. 8A  FIG. 8B  FIG. 8C  FIG. 8D  FIG. 8E  FIG. 8F  FIG. 8G

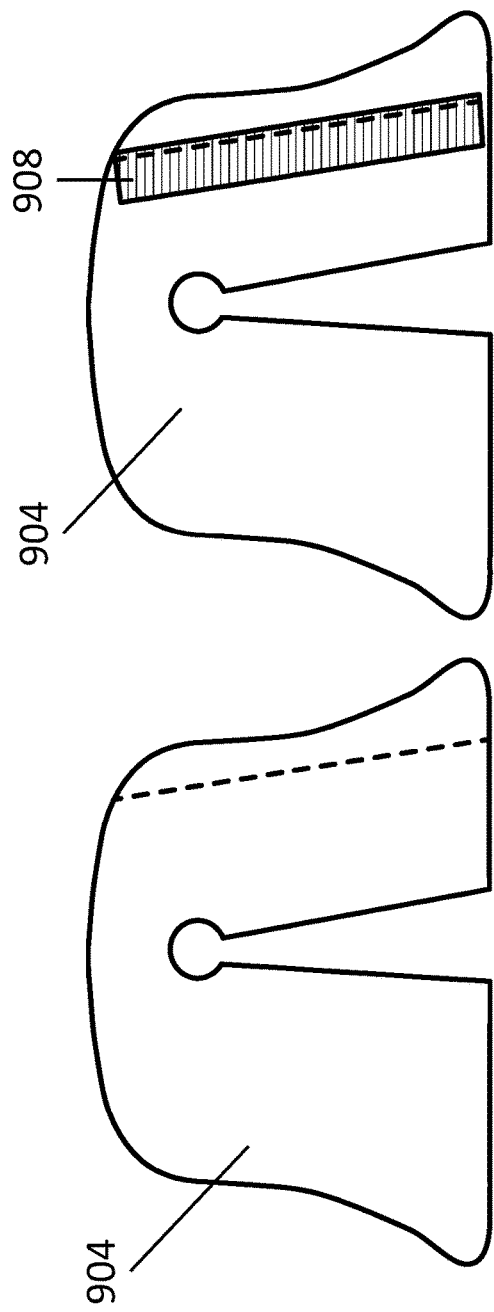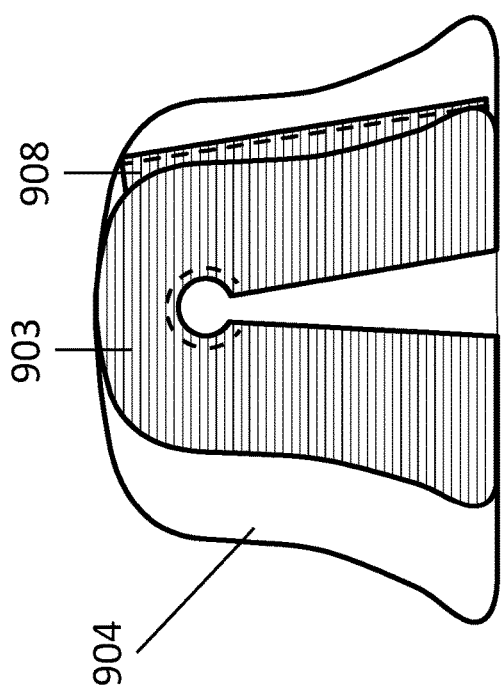

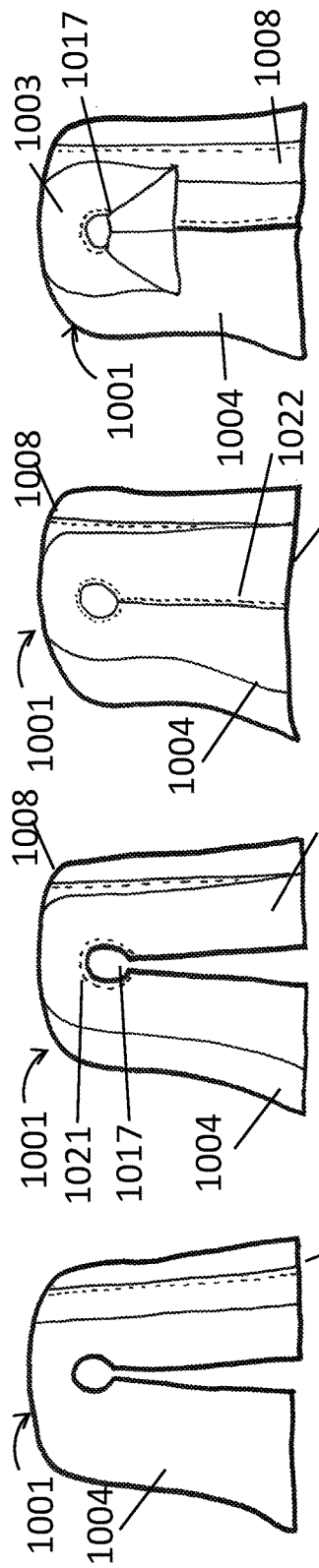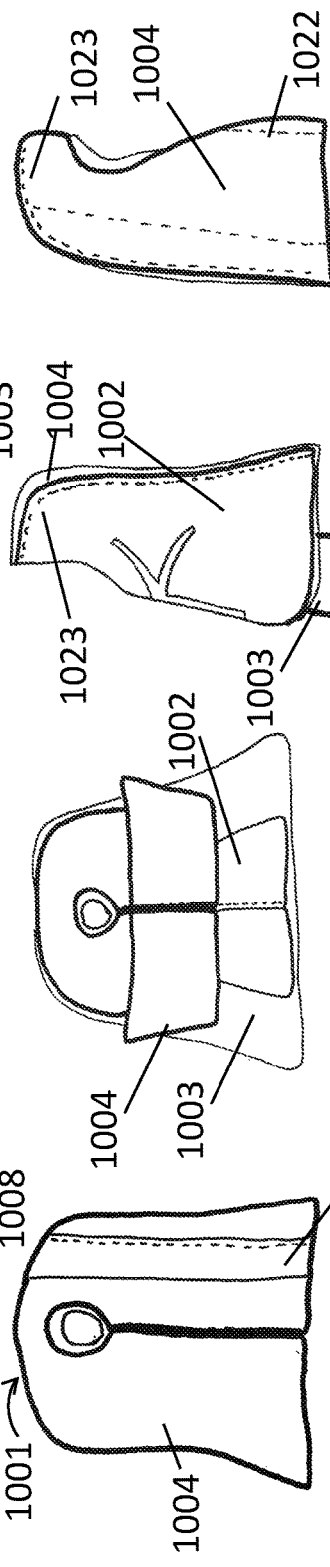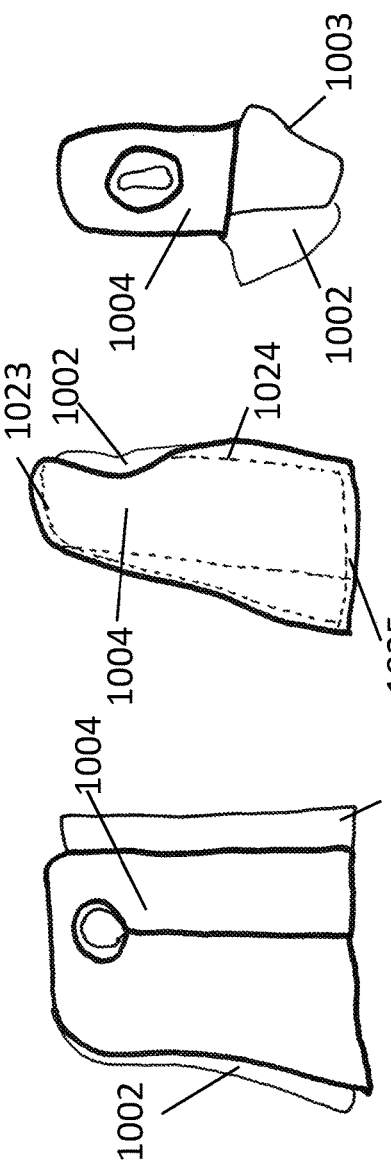

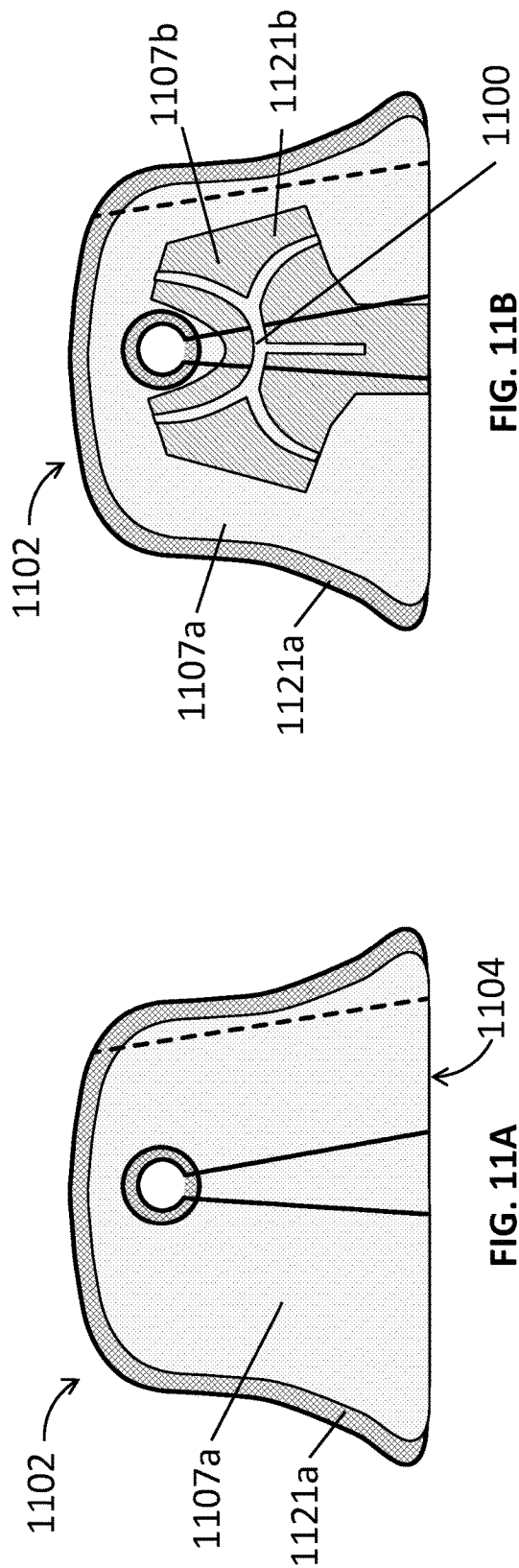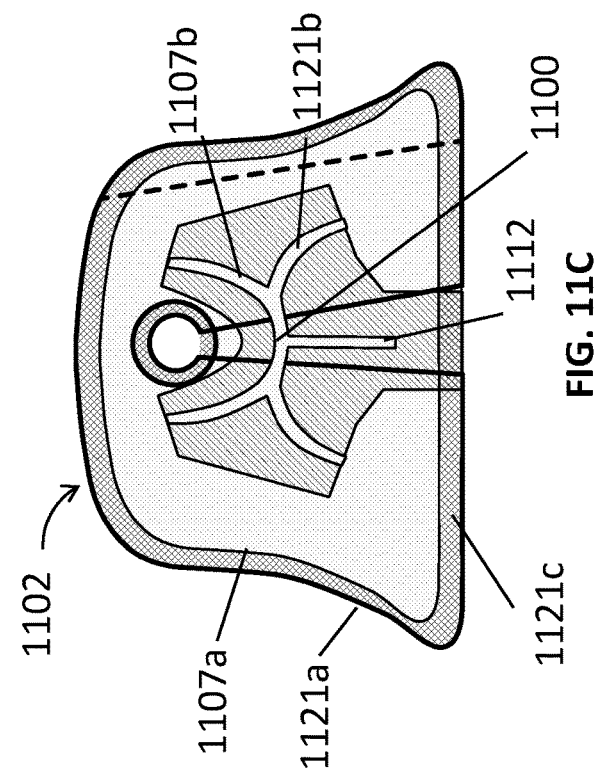

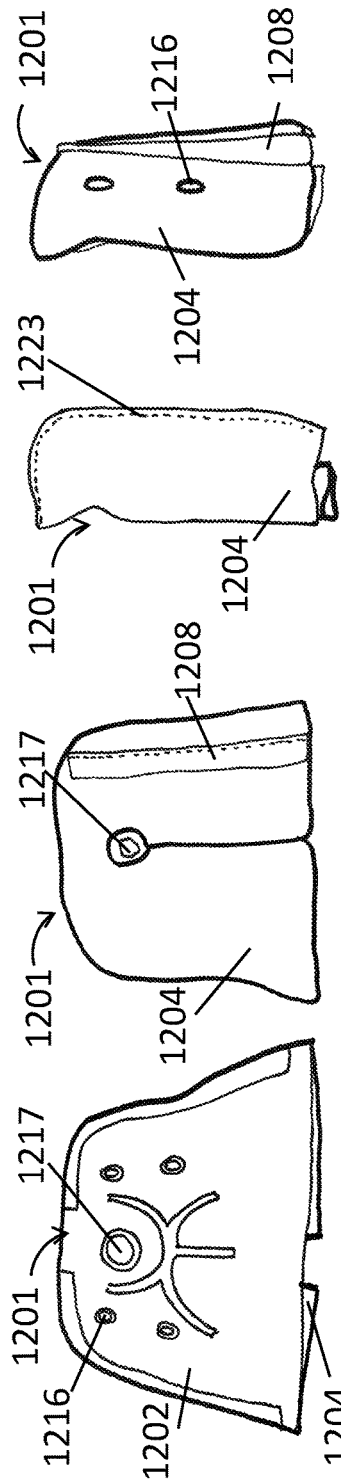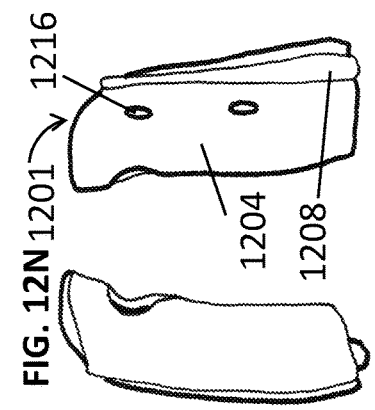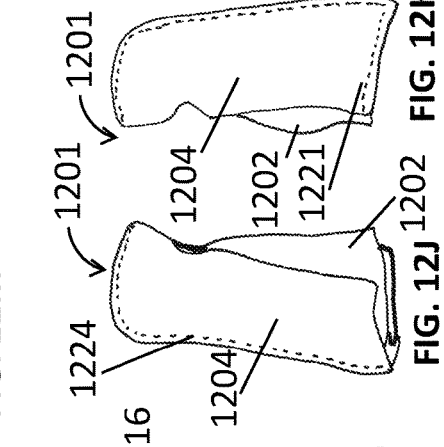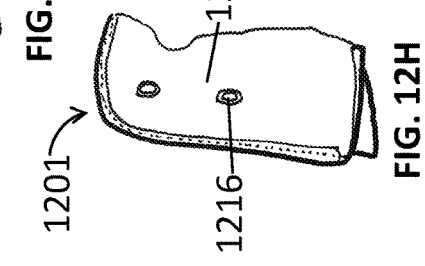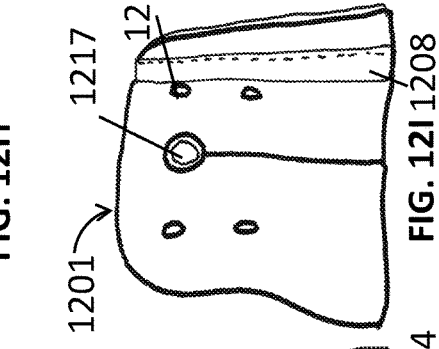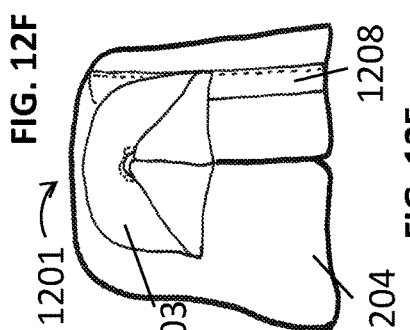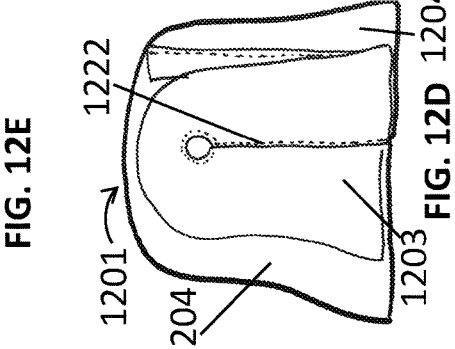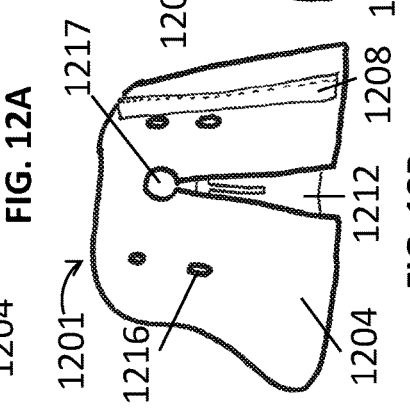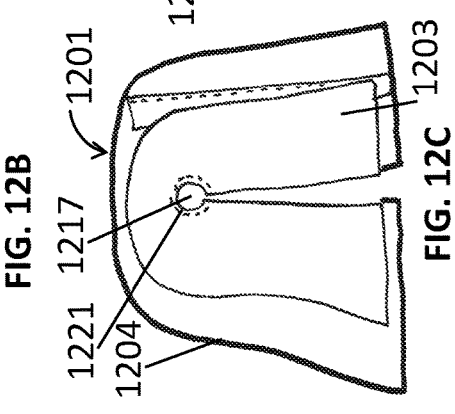

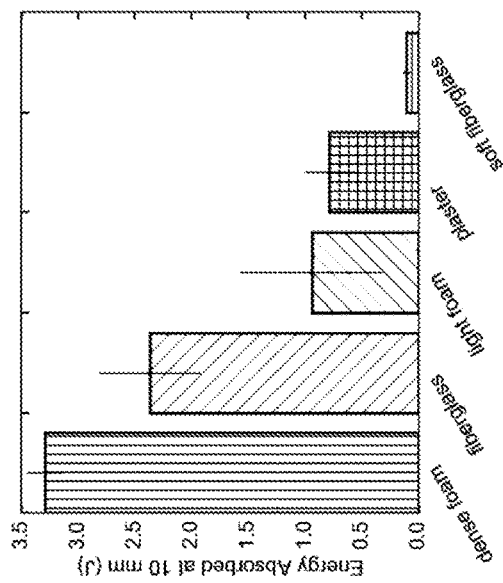
FIG. 17B
FIG. 17C
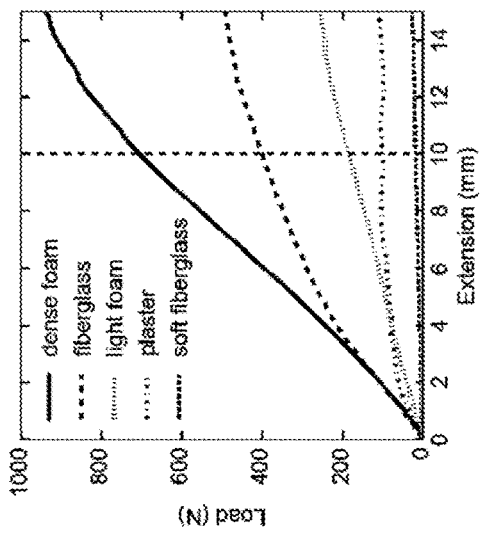
FIG. 17A
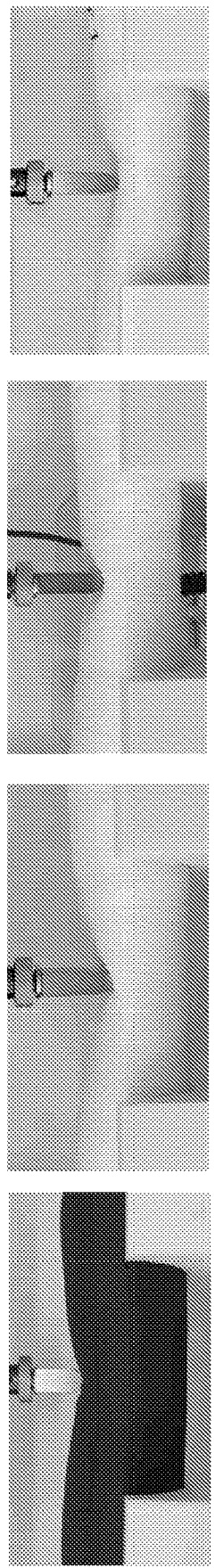
FIG. 17G
FIG. 17F
FIG. 17E
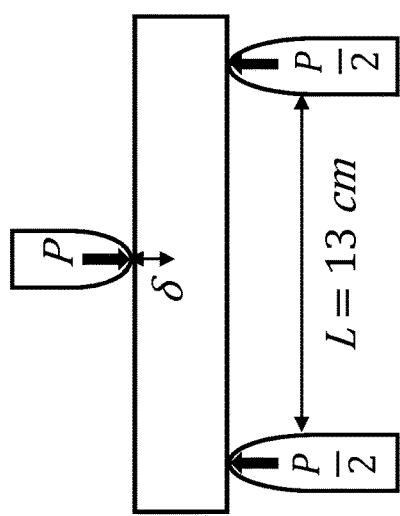
FIG. 17D

EXPANDING FOAM-FABRIC ORTHOPEDIC LIMB STABILIZATION DEVICE

RELATED APPLICATIONS

This application is a 35 U.S.C. § 371 National Phase Entry Application of International Application No. PCT/US2020/56625, filed on Oct. 21, 2020. International Application No. PCT/US2020/56625 designates the U.S. and claims the benefit of priority under 35 U.S.C. § 119 to U.S. Provisional Application Ser. No. 62/923,938, filed Oct. 21, 2019, the contents of which are incorporated by reference.

COPYRIGHT NOTICE

This patent disclosure may contain material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This application relates to an orthopedic limb stabilization device. In particular, this application relates to an expanding foam-fabric orthopedic limb stabilization device.

BACKGROUND

Limb stabilization devices are challenging to apply in the field. Many limb stabilization devices, including plaster and fiberglass casts require expertise to apply or mold and are susceptible to user error. Additionally, limb stabilization devices may require use of infrastructure such as imaging or three-dimensional printing not available in the field. Such devices must provide sufficient stiffness to stabilize a limb, but must also be formed at sufficiently low temperatures to avoid burning a patient. As a result, it is challenging to design limb stabilizing devices using thermoplastic materials that are moldable at low temperatures but not susceptible to creep. Limb stabilization devices also provide challenges for hygiene because they are not readily removed. Removal of plaster and fiberglass casts is performed using oscillatory saws that can frighten or burn a patient.

SUMMARY

In one aspect, a kit includes a sleeve including an outer lining and an inner lining; a pouch arranged within the sleeve and including one or more polymer sheets, a plurality of channels, and a plurality of vents; and a foam precursor capable of forming a foam within the pouch.

In one embodiment, the outer lining includes a knit textile, a woven textile, a stretchable woven textile, a nonwoven textile, or combinations thereof.

In one embodiment, the outer lining includes a polyester, nylon, cotton, linen, rayon, viscose, lyocell, silk, wool, aramid fibers, polypropylenes, polyolefins, carbon fibers, acrylic, spandex, or combinations thereof.

In one embodiment, the outer lining is a laminate sheet including a polymer layer and a textile selected from the group consisting of a knit textile, a woven textile, a stretchable woven textile, a nonwoven textile, and combinations thereof.

In one embodiment, the polymer layer includes a thermoplastic polymer selected from the group consisting of polyurethanes, polysiloxanes, poly(vinyl chloride), styrene-butadiene-styrene or polystyrene-ethylene-butylene-styrene block copolymers, and combinations thereof.

In one embodiment, the outer lining is stiffer than the inner lining.

In one embodiment, the inner lining is a knit spacer fabric or an open-celled, soft polymer foam.

In one embodiment, the inner lining is pre-strained.

In one embodiment, inner lining is pre-strained longitudinally.

In one embodiment, the inner lining includes polyester, spandex, nylons, cotton, linen, rayon, viscose, lyocell, silk, wools, aramid fibers, polypropylenes polyolefins, acrylic, carbon fiber, and combinations thereof.

In one embodiment, the sleeve includes an overlapping panel.

In one embodiment, the pouch is formed by heat bonding.

In one embodiment, the one or more polymer sheets are impermeable.

In one embodiment, the one or more polymer sheets include thermoplastic polymers.

In one embodiment, the total resistance of each of the plurality of channels is equal.

In one embodiment, the plurality of channels have a common inlet.

In one embodiment, the plurality of channels each includes an outlet.

In one embodiment, the diameter of each of the plurality of channels decreases at the outlet.

In one embodiment, each of the plurality of channels are branched at the outlet.

In one embodiment, the plurality of channels are configured to deliver the foam precursor to each corner of the pouch.

In one embodiment, the plurality of channels are configured such that the plurality of channels are oriented downwards when the foam precursor is injected.

In one embodiment, the plurality of vents have a greater density at the center of the pouch.

In one embodiment, the plurality of vents each have a diameter of less than about 0.001 inches.

In one embodiment, the kit includes a plurality of ventilation holes in the pouch and the sleeve.

In one embodiment, the foam precursor includes a first component and a second component capable of forming the foam when mixed together.

In one embodiment, the foam includes a polyurethane or epoxy-based foam.

In one embodiment, foam precursor forms the foam within about 1 to 10 minutes.

In one embodiment, the pouch includes a squeezable pouch containing the foam precursor, wherein the squeezable pouch is configured to release the foam precursor.

In one embodiment, the squeezable pouch is disposed within the pouch.

In one embodiment, the squeezable pouch is disposed exterior to the pouch.

In one embodiment, the pouch includes a first squeezable pouch containing the first component and a second squeezable pouch containing the second component, wherein the first and second squeezable pouches are configured to release the first and second components such that the first and second components mix together.

In one aspect, a method of stabilizing a body part includes providing a sleeve including an outer lining and an inner lining around a body part; providing a pouch arranged within the sleeve and including one or more polymer sheets, a plurality of channels, and a plurality of vents; providing a foam precursor in the pouch; and forming a foam within the pouch.

In one embodiment, providing a sleeve includes sewing the inner lining to the outer lining.

In one embodiment, providing a sleeve includes pre-straining the inner lining.

In one embodiment, providing the pouch includes heat sealing the first polymer sheet.

In one embodiment, providing a foam precursor includes injecting the foam precursor into the pouch through the plurality of channels.

In one embodiment, providing a foam precursor includes releasing the foam precursor from a squeezable pouch.

In one embodiment, the foam precursor includes a first component and a second component capable of forming a foam when mixed together.

In one embodiment, providing the foam precursor includes injecting the first component and the second component into the pouch through the plurality of channels.

In one embodiment, providing the foam precursor includes releasing the first component from a first squeezable pouch and releasing the second foam precursor from a squeezable pouch.

In one embodiment, the method includes molding the foam precursor as the foam precursor form the foam.

In one embodiment, the method includes removing the sleeve by cutting the sleeve.

BRIEF DESCRIPTION OF THE DRAWINGS

The objects and advantages will be apparent upon consideration of the following detailed description, taken in conjunction with the accompanying drawings, in which like reference characters refer to like parts throughout, and in which:

FIG. 2A shows a lateral view of a radiograph of a model arm with an expanding foam-fabric orthopedic limb stabilization device, according to certain embodiments.

FIG. 2B shows an anterior view of a radiograph of a model arm an expanding foam-fabric orthopedic limb stabilization device, according to certain embodiments.

FIG. 2C shows computed tomography images at transverse sections of a model arm with an expanding foam-fabric orthopedic limb stabilization device at three locations, according to certain embodiments.

FIG. 2D shows computed tomography images at transverse sections of a model arm with an expanding foam-fabric orthopedic limb stabilization device with a prestrained inner lining at three locations, according to certain embodiments.

FIG. 3 shows a pouch with pressure vents, according to certain embodiments.

FIG. 4A shows channels in a pouch, according to certain embodiments.

FIG. 4B shows a photograph of foam precursors being injected into an expanding foam-fabric orthopedic limb stabilization device with a sleeve, according to certain embodiments.

FIG. 4C shows a photograph of an expanding foam-fabric orthopedic limb stabilization device with a sleeve after formation of a foam, according to certain embodiments.

FIG. 4D shows a photograph of foam precursors being injected into a pouch of an expanding foam-fabric orthopedic limb stabilization device, according to certain embodiments.

FIG. 4E shows a photograph of a pouch of an expanding foam-fabric orthopedic limb stabilization device after formation of a foam, according to certain embodiments.

FIG. 6A shows fabrication of a pouch with squeezable pouches for a foam precursor component A and a foam precursor component B, according to certain embodiments.

FIG. 6B shows storage of a foam precursor component A and a foam precursor component B in squeezable pouches, according to certain embodiments.

FIG. 6C shows mixing a foam precursor component A and a foam precursor component B in squeezable pouches, according to certain embodiments.

FIG. 8A shows a pattern of an outer lining of a sleeve, according to certain embodiments.

FIG. 8B shows a pattern of a polymer sheet of a pouch, according to certain embodiments.

FIG. 8C shows a cover sheet for fabrication of a pouch, according to certain embodiments.

FIG. 8D shows a pattern for an inner lining of a sleeve, according to certain embodiments.

FIG. 8E shows a polymer sheet for fabrication of channels in a pouch, according to certain embodiments.

FIG. 8F shows a cover sheet for fabrication of channels in a pouch, according to certain embodiments.

FIG. 8G shows a band for an overlapping panel of a sleeve, according to certain embodiments.

FIG. 9A shows an outer lining of a sleeve, according to certain embodiments.

FIG. 9B shows a fabric band sewn onto an outer lining of a sleeve, according to certain embodiments.

FIG. 9C shows an inner lining sewn to an outer lining of a sleeve, according to certain embodiments.

FIG. 10A shows the outer lining of the sleeve cut into a pattern during manufacturing of the limb stabilization device, according to certain embodiments.

FIG. 10B shows a sleeve after sewing a first seam during manufacturing of the limb stabilization device, according to certain embodiments.

FIG. 10C shows a sleeve after sewing a second and third seam during manufacturing of the limb stabilization device, according to certain embodiments.

FIG. 10D shows a first inversion step during manufacturing of the limb stabilization device, according to certain embodiments.

FIG. 10E shows a sleeve after a first inversion step during manufacturing of the limb stabilization device, according to certain embodiments.

FIG. 10F shows a sleeve after inserting a pouch during manufacturing of the limb stabilization device, according to certain embodiments.

FIG. 10G shows a sleeve after sewing a fourth seam during manufacturing of the limb stabilization device, according to certain embodiments.

FIG. 10H shows a second inversion step during manufacturing of the limb stabilization device, according to certain embodiments.

FIG. 10I shows a sleeve after a second inversion step during manufacturing of the limb stabilization device, according to certain embodiments.

FIG. 10J shows a sleeve after sewing a fifth, sixth, and seventh seam during manufacturing of the limb stabilization device, according to certain embodiments.

FIG. 10K shows a third inversion step during manufacturing of the limb stabilization device, according to certain embodiments.

FIG. 10L shows a completed sleeve after a third inversion step during manufacturing of the limb stabilization device, according to certain embodiments.

FIG. 11A shows bonding of a polymer sheet to an outer lining to form a pouch, according to certain embodiments.

FIG. 11B shows bonding of polymer sheets to form channels of a pouch, according to certain embodiments.

FIG. 11C shows bonding of a polymer sheets to form a pouch, according to certain embodiments.

FIG. 12A shows one side of a pouch with ventilation holes bonded to a sleeve with ventilation holes during manufacturing of the limb stabilization device with ventilation holes, according to certain embodiments.

FIG. 12B shows the opposite side of a pouch with ventilation holes bonded to a sleeve with ventilation holes during manufacturing of the limb stabilization device with ventilation holes, according to certain embodiments.

FIG. 12C shows the exterior and inner linings of the sleeve cut into a pattern during manufacturing of the limb stabilization device with ventilation holes, according to certain embodiments.

FIG. 12D shows a sleeve after sewing a first, second, and third seam during manufacturing of the limb stabilization device with ventilation holes, according to certain embodiments.

FIG. 12E shows a first inversion step during manufacturing of the limb stabilization device with ventilation holes, according to certain embodiments.

FIG. 12F shows a sleeve after a first inversion step during manufacturing of the limb stabilization device with ventilation holes, according to certain embodiments.

FIG. 12G shows a sleeve after sewing a fourth seam during manufacturing of the limb stabilization device with ventilation holes, according to certain embodiments.

FIG. 12H shows a second inversion step during manufacturing of the limb stabilization device with ventilation holes, according to certain embodiments.

FIG. 12I shows a sleeve after a second inversion step during manufacturing of the limb stabilization device with ventilation holes, according to certain embodiments.

FIG. 12J shows a sleeve after sewing a fifth seam during manufacturing of the limb stabilization device with ventilation holes, according to certain embodiments.

FIG. 12K shows a sleeve after sewing a sixth and seventh seam during manufacturing of the limb stabilization device with ventilation holes, according to certain embodiments.

FIG. 12L shows a third inversion step during manufacturing of the limb stabilization device with ventilation holes, according to certain embodiments.

FIG. 12M shows a third inversion step during manufacturing of the limb stabilization device with ventilation holes, according to certain embodiments.

FIG. 12N shows a sleeve after a third inversion step during manufacturing of the limb stabilization device with ventilation holes, according to certain embodiments.

FIG. 17A shows a schematic of a three-point bending test, according to certain embodiments.

FIG. 17B shows force-extension curves for tubes of materials loaded in three-point bending, according to certain embodiments.

FIG. 17C shows a graph of energy absorbed by tubes of materials loaded in three-point bending, according to certain embodiments.

FIG. 17D shows deformation of a light foam loaded in three-point bending, according to certain embodiments.

FIG. 17E shows deformation of a fiberglass tube loaded in three-point bending, according to certain embodiments.

FIG. 17F shows deformation of a plaster tube loaded in three-point bending, according to certain embodiments.

FIG. 17G shows deformation of a soft fiberglass tube loaded in three-point bending, according to certain embodiments.

DETAILED DESCRIPTION

In one aspect, an expanding foam-fabric orthopedic limb stabilization device includes a sleeve with an outer lining and an inner lining, an internal pouch arranged within the sleeve and including one or more polymer sheets, a plurality of channels, and a plurality of pressure vents; and a foam precursor capable of forming a foam within the pouch.

In some embodiments, an expanding foam-fabric orthopedic limb stabilization device employs a reactive injection molding process with an expanding polymer foam to form a precise-fitting, rigid structure within a matter of minutes. This limb stabilization device provides sufficient mechanical stabilization and a safe application and removal process. In addition, this limb stabilization device is water-resistant, radiolucent, lightweight, comfortable and hygienic. In some embodiments, an expanding and solidifying foam is contained within a fabric garment or sleeve worn on the human body, designed to (i) ensure uniform expansion of the foam, (ii) promote patient comfort during use, (iii) be removed simply with a pair of scissors, and (iv) be manufactured using standard processes from the garment industry. By using a foaming reaction, liquid precursors undergo a simultaneous expansion and solidification process, such that the resulting foam molds to the shape of the object that constrains its expansion (i.e. a foam-in-place process).

Figure 1B:
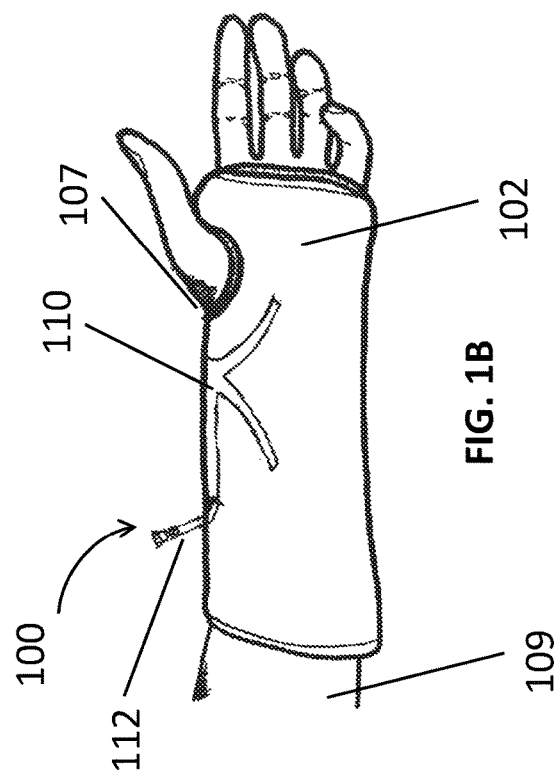
FIG. 1B shows an internal pouch of an expanding foam-fabric orthopedic limb stabilization device, according to certain embodiments.
Figure 1D:
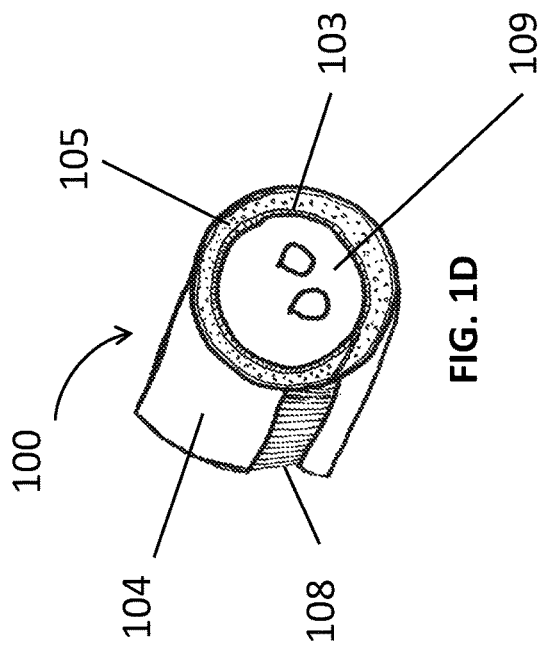
FIG. 1D shows a transverse cross-section of an expanding foam-fabric orthopedic limb stabilization device, according to certain embodiments.
Figure 1A:
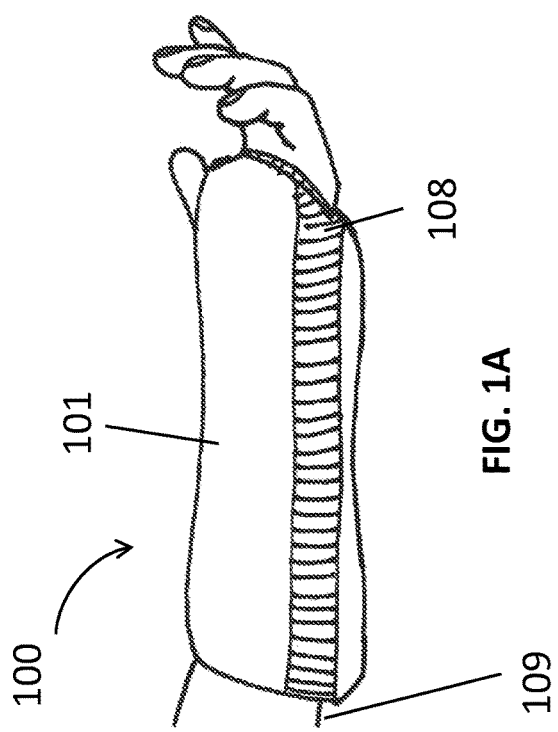
FIG. 1A shows an expanding foam-fabric orthopedic limb stabilization device, according to certain embodiments.
Figure 1C:
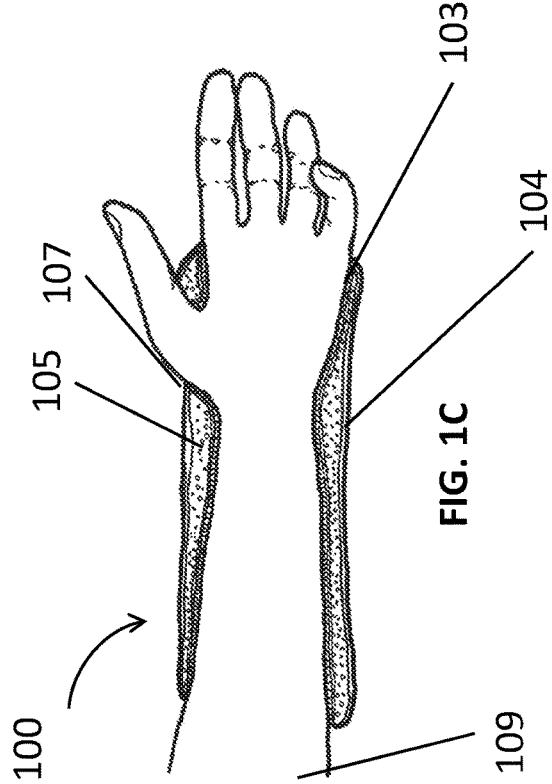
FIG. 1C shows a longitudinal cross-section of an expanding foam-fabric orthopedic limb stabilization device, according to certain embodiments.

In some embodiments, shown in FIGS. 1A-1D, an expanding foam-fabric orthopedic limb stabilization device 100 includes a sleeve 101, shown in FIG. 1A, and a pouch 102, shown in FIG. 1B, arranged within the sleeve 101. FIGS. 1A-1D show an exemplary embodiment where the limb 109 is a wrist. In this embodiment, the device 100 includes a thumbhole 107. In some embodiments, shown in the cross-section views of FIGS. 1C (longitudinal) and 1D (transverse), the sleeve 101 is a textile sleeve formed by an inner lining 103 and an outer lining 104. In some embodiments, shown in FIGS. 1A and 1D, the sleeve includes an overlapping panel or fabric band 108 for removal. In some embodiments, the pouch 102 is formed by one or more polymer sheets bonded together. In some embodiments, shown in FIG. 1B, the pouch includes and inlet 112 and a channel network 110 for distribution of the foam. In some embodiments, shown in FIGS. 1C and 1D, the stabilization device includes a foam 105 within the pouch 102 after deployment. In some embodiments, the pouch 102 distributes and contains the foam 105 within the pouch 102. In some embodiments, the foam pouch distributes the foam uniformly. In some embodiments, the stabilization device is deployed by delivering one or more foam precursors 106 into the pouch 102, where the precursors 106 are distributed and form the foam 105. In some embodiments, the stabilization device is deployed by injecting one or more foam precursors 106 into the pouch 102, where the precursors 106 are distributed and form the foam 105. In some embodiments, the stabilization device is deployed by releasing one or more foam precursors 106 from a squeezable pouch within the pouch 102, where the precursors 106 are distributed and form the foam 105.

Figure 1G:
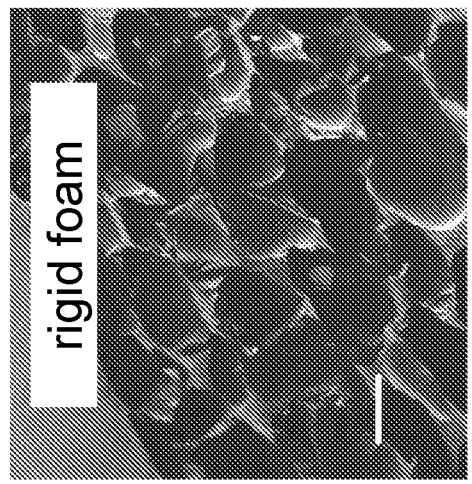
FIG. 1G shows an SEM image of a foam of an expanding foam-fabric orthopedic limb stabilization device, according to certain embodiments.
Figure 1F:
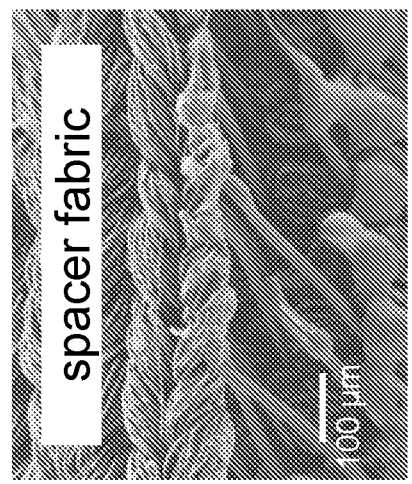
FIG. 1F shows an SEM image of an inner lining of a sleeve an expanding foam-fabric orthopedic limb stabilization device, according to certain embodiments.
Figure 1E:
FIG. 1E shows an SEM image of an outer lining of a sleeve of an expanding foam-fabric orthopedic limb stabilization device, according to certain embodiments.

FIGS. 1E-1G show SEM images of exemplary components of an expanding foam-fabric orthopedic limb stabilization device. FIG. 1E shows an SEM image of an exemplary outer lining made of a polyester-thermoplastic polyurethane laminate. FIG. 1F shows an SEM image of an exemplary inner lining made of a knit spacer fabric. FIG. 1G shows an SEM image of an exemplary closed-cell polyurethane foam.

In some embodiments, shown in FIGS. 2A-2D, an expanding foam-fabric orthopedic limb stabilization device is radiolucent to allow a doctor to monitor a healing limb. FIGS. 2A and 2B show radiographs of the limb stabilization device. FIGS. 2C-2D show x-ray computed tomography sections of the limb stabilization device.

Materials

In some embodiments, the sleeve is a textile sleeve including an outer lining and an inner lining. In some embodiments, the sleeve includes an overlapping fabric panel or band for removal. In some embodiments, the fabric panel is approximately 1 cm wide and overlaps the sleeve on one side of the limb allow for removal with scissors rather than an oscillatory saw. In some embodiments, this overlap ensures circumferential cast coverage because there is foam protection of the fractured bone beneath this panel. In some embodiments, the sleeve can be sewn using manufacturing processes from the garment industry.

In some embodiments, the outer lining of the sleeve is a textile material. In some embodiments, the outer lining is liquid resistant and comfortable to the touch. In some embodiments, the outer lining is stiffer than the inner lining. In some embodiments, the textile is a knit textile. In some embodiments, the textile is a stretchable knit textile. Non-limiting examples of textiles for the outer lining include knits, wovens, stretchable wovens, nonwovens and combinations thereof. Non-limiting examples of textile materials include polyesters, nylons, cotton, linen, rayons or viscose, lyocell, spandex, silk, wools, aramid fibers such as Kevlar and Nomex, polypropylenes, polyolefins, acrylic, and carbon fiber either a homogenous material or a blends. In one embodiment, the textile is a blend of 95% nylon and 5% spandex. In some embodiments, the knit textiles are warp or weft knit. Non-limiting examples of woven constructions include plain weave, basket weave, twill, velvet, velveteen, satin, sateen, terrycloth, and combinations thereof. In some embodiments, the outer lining is a laminate including a textile and a polymer coating. In some embodiments, a laminate enables bonding of the outer lining to an interior thermoplastic pouch. In some embodiments, bonding the laminate of the outer lining to the thermoplastic pouch enables formation of venting pouches. In some embodiments, a laminated film provides protection from foam escaping from pressure vents in the pouch. In some embodiments, the laminate includes any of the aforementioned textiles. In some embodiments, the laminate includes a thermoplastic polymer. In some embodiments, the laminate includes a thermoplastic elastomer. Non-limiting examples of polymer sheets in the laminate include those made from polyurethane, polysiloxane, poly(vinyl chloride), styrenebutadiene-styrene, polystyrene-ethylene-butylene-styrene block copolymers, and combinations thereof. In some embodiments, a laminate includes a thermoplastic elastomer and a knit textile. In some embodiments, a laminate includes a thermoplastic polymer and a woven fabric. Non-limiting examples of laminates include polyester knit with a thermoplastic polyurethane coating, nylon woven with a polysiloxane coating, and polyester woven with a polytetrafluoroethylene coating.

In some embodiments, the inner lining is a textile. In some embodiments, the inner lining is a stretchable, breathable knit spacer fabric. In some embodiments, the inner lining contains an anti-microbial coating to assist in the maintenance in hygiene. In some embodiments, the anti-microbial coating includes agents such as quaternary ammonium compounds, triclosan, metal salts, and polybiguanides, and other naturally derived chemicals such as terpenoids, coumarins, tannins, and flavonoids. In some embodiments, the inner lining is a knit spacer created by connecting two independently knit fabric with spacer yarns. In this embodiment, the knit spacer fabric has a compressible 3D structure, superior breathability in all directions, and a hollow nature that effectively thermally insulates the skin from the exothermic foam process and lowers the magnitude of the temperature to which the skin is exposed. In some embodiments, the inner lining is pre-strained prior to assembly of the sleeve to avoid wrinkling during deployment of the foam. For example. FIG. 2C shows an inner lining that was not pre-strained prior to assembly and formed wrinkles, indicated by asterisks. In contrast, FIG. 2D shows an inner lining that was pre-strained prior to assembly and did not form wrinkles. In some embodiments, the inner lining is smaller than the outer lining or the inner lining is pre-strained longitudinally. In some embodiments, the inner lining is selected to wick water vapor or transport air. In some embodiments, the inner lining is a blend of synthetic knit textiles. Non-limiting examples of textile fibers for the inner lining include polyester, spandex, nylons, cotton, linen, rayons or viscose, lyocell, silk, wools, aramid fibers such as Kevlar and Nomex, polypropylenes polyolefins, acrylic, and carbon fiber either a homogenous material or a blend. In some embodiments the inner lining includes a 90% polyester/10% spandex blend. In some embodiments, the inner lining is an open-celled, soft polymer foam.

In some embodiments, shown in FIG. 3, the pouch 302 is formed by one or more polymer sheets. In some embodiments, the pouch guides distribution of foam precursors and foam expansion. In some embodiments, the polymer sheets are thermoplastic polymer sheets. In some embodiments, the polymer sheets are heat bonded at the perimeter of the pouch. In some embodiments, the polymer sheets are capable of being heat bonded at 90-200° C. In some embodiments, the polymer sheets are capable of being heat bonded at 90° C., 100° C., 110° C., 120° C., 130° C., 140° C., 150° C., 160° C., 170° C., 180° C., 190° C., 200° C., or any temperature in between. In some embodiments, the heat bonding temperature depends on the glass transition temperature of a glassy block of a copolymer, which serves as physical cross-links in the operating state to endow the material with elastomeric behavior. In some embodiments, the pouch is impermeable to avoid leaking of foam precursors. In some embodiments, the pouch protects the patient from contact with the foam precursors. Non-limiting examples of polymer sheets include thermoplastic elastomers such Stretchlon®, poly(urethane), polysiloxane, styrene-butadiene-styrene, polystyrene-ethylene-butylene-styrene block copolymers and combinations thereof. For example, Stretchlon® is described in U.S. Pat. No. 5,123,985, the contents of which are hereby incorporated by reference. In some embodiments, the polymer sheets have a thickness of about 0.0005-0.05 inches. In some embodiments the polymer sheets have a thickness of about 0.0005 inches, 0.001 inches, 0.0015 inches, 0.0020 inches, 0.0025 inches, 0.0030 inches, 0.0035 inches, 0.0040 inches, 0.0045 inches, 0.005 inches, 0.010 inches, 0.015 inches, 0.020 inches, 0.025 inches, 0.030 inches, 0.035 inches, 0.040 inches, 0.045 inches, 0.050 inches. In some embodiments, the polymer sheets are not tacky or sticky. In some embodiments, the sheets have a high elongation In some embodiments, shown in FIG. 3, the pouch 302 includes pressure vents 314 for release of gas that is produced during the foam formation process. In some embodiments, the pressure vents act as a pressure-venting system, avoiding build-up of pressure in the pouch. In some embodiments, pressure vents prevent the formation of larger air bubbles which would cause a buildup of pressure and inhibit the uniform distribution of the foam. In some embodiments, the pressure vents are sized to allow gas out but to prevent leaking of viscous foam precursors. In some embodiments, the pressure vents have diameters between 0.0008 and 0.0012 inches. In some embodiments, the pressure vents have diameters of 0.0008 inches, 0.001 inches, 0.0012 inches, or any value in between. In some embodiments, the pressure vents are located in the polymer layer of the pouch facing away from the limb because gas rises due to gravity and in case any precursor liquid bubbles through the pressure vents in small quantities. In some embodiments, the pouch includes a region 315 with a higher density of pressure vents. In some embodiments, the high density region is greatest at the center of the pouch. In some embodiments, the high density region is in a region of the pouch that will be facing upwards during deployment of the foam precursors and foam formation. In these embodiments, a combination of gravity and fluid dynamics helps gas reach the high density region for venting. In some embodiments, the density of pressure vents is about 1 vent per square inch. In some embodiments, the density of vents in a high density region is about 3-5 vents per square inch In some embodiments, shown in FIGS. 4A-6D, the pouch includes a network 410 of channels for distribution of foam precursors and foam. In some embodiments, channels are formed by heat bonding a polymer sheet to one of the polymer sheets of the pouch. In some embodiments, shown in FIG. 4A the network of channels includes a common inlet 412, a plurality of channels 411a, 411b, 411c, 411d in fluid connection with the inlet, and an outlet 413a, 413b, 413c, 413d for each channel. In some embodiments, the channels are curved.

In some embodiments, the channels are designed so that the total resistance for the path of each channel is equivalent. In these embodiments, equal resistance results in equal flow along each channel. In this way, foam precursors are distributed evenly through the channels. In some embodiments, the width of the channels is determined by specifying the lengths of the branching channels, assuming Hagen-Poiseuille flow and solving for the set of fluidic resistances, $\{R1\text{-}R3\}$ [N·s/m$^5$] that would yield equivalent flow rates, Q [m$^3$/s], at each outlet. Assuming Poiseuille flow, the approximate fluidic resistance of each channel is given by $$R = \Delta P/Q = 8\pi^3 \mu l/w^4$$

where is the fluidic resistance, $\Delta P$ is the pressure difference, Q is the flowrate, $\mu$ is the viscosity of the foaming liquid, l is the length of the channel, and w is the width of the channel.

In some embodiments, the channel geometries are optimized empirically to ensure uniform foam distribution. In some embodiments, the fluidic resistance of the channels to the injection of the foam precursors is in the range 0.2-2 kPa s/cm$^3$. In some embodiments, the fluidic resistance is 0.2 kPa/cm$^3$, 0.4 kPa/cm$^3$, 0.6 kPa/cm$^3$, 0.8 kPa/cm$^3$, 1.0 kPa/cm$^3$, 1.2 kPa/cm$^3$, 1.4 kPa/cm$^3$, 1.6 kPa/cm$^3$, 1.8 kPa/cm$^3$, 2.0 kPa/cm$^3$, or any value in between. In some embodiments, the channels have widths between 0.5-1.0 cm. In some embodiments, the channels have widths of 0.5 cm, 0.6 cm, 0.7 cm, 0.8 cm, 0.9 cm, 1.0 cm, or any value in between. In some embodiments, there is a channel leading to each corner of the pouch such that foam is delivered to each corner of the pouch. In some embodiments, there are four channels. In some embodiments, the channels are branched at each outlet.

In some embodiments, the channels have tapered ends (i.e., the diameter of each of the plurality of channels decreases at the outlet) such that resistance is highest at the outlets of the channels. In these embodiments, when foam precursors reach the end of a channel, the resistance increases in that channel, causing a lower relative resistance at other channels so that foam precursors are more likely to enter those channels. This decreases the likelihood that the liquid precursors would flow out of one channel before to reaching the ends of other channels. In this way foam precursors are distributed evenly through the channels and throughout the pouch.

In some embodiments, shown in FIGS. 4B-4E, each channel 411a, 411b, 411c, 411d is oriented such that its outlet 413a, 413b, 413c, 413d faces downwards when the foam precursors are deployed. In this embodiment, gravity helps distribute the foam precursors. FIG. 4B shows a photograph of foam precursors being injected through an inlet 412 into an expanding foam-fabric orthopedic limb stabilization device with a sleeve 401. FIG. 4C shows a photograph of an expanding foam-fabric orthopedic limb stabilization device with a sleeve 401 after formation of a foam. FIGS. 4D-4E show delivery of precursors without the sleeve so that it is possible to see the pouch 402 and the orientation of the channels 411a, 411b and outlets 413a, 413b during deployment. FIG. 4D shows a photograph of foam precursors being injected through an inlet 412 into a pouch 402 of an expanding foam-fabric orthopedic limb stabilization device. FIG. 4E shows a photograph of a pouch 402 of an expanding foam-fabric orthopedic limb stabilization device after formation of a foam. As seen in FIGS. 4D-4E, the channels 411a, 411b are facing downwards during deployment.

In some embodiments, the foam is formed by one or more precursors. In some embodiments, the foam precursor includes a first precursor component and a second precursor component that form a foam when mixed together. Non-limiting examples of precursors are Methylene diphenyl isocyanate-based prepolymers (i.e., having a functionality of 2) and polyols (e.g., polyether polyol having a functionality of 3). In some embodiments, polyols have the following components 1) a catalyst (e.g., N,N,N,N,N-penta methyl diethylene triaminec (PMDETA), or diazobicyclo[2.2.2]octane), 2) a surfactant (e.g., polyether dimethylsiloxane), and 3) distilled water as a "blowing agent." In some embodiments, a poly urethane foam is formed from a single component precursor. In some embodiments, a reaction is initiated by mixing. In other embodiments, a reaction is initiated by using a temperature-activated single-component foam and activating with heat. In some embodiments, activating with heat includes activating with a resistive heating circuit. A resistive heating circuit can include battery, a patterned resistive film on thermoplastic pouch, and an electrical switch.

Figure 5A:
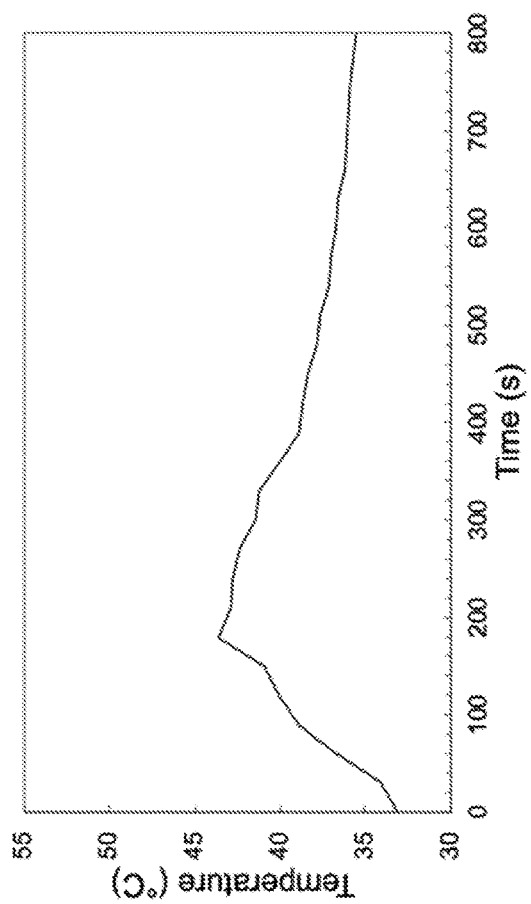
FIG. 5A shows the temperature as a function of time after injection of foam precursors into an expanding foam-fabric orthopedic limb stabilization device, according to certain embodiments.
Figure 5B:
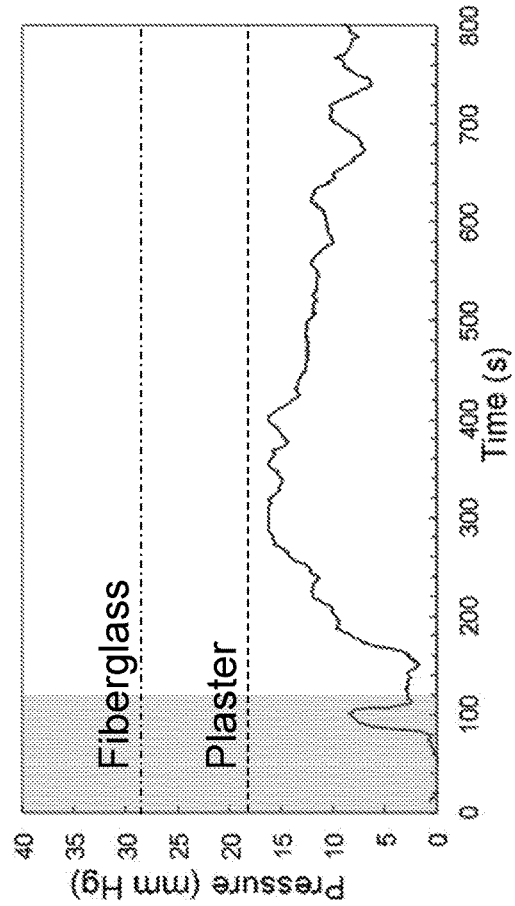
FIG. 5B shows the pressure exerted by a foam as a function of time after injection of foam precursors into an expanding foam-fabric orthopedic limb stabilization device, according to certain embodiments.

In some embodiments, heat is released during foam formation. In some embodiments, the temperature is minimized to mitigate risk of thermal injuries or burns. As shown in FIG. 5A, during formation of an exemplary polyurethane foam in a limb stabilization device, the temperature remains below 45° C., below the typical temperature for application of a plaster or fiberglass cast. In some embodiments, the temperature during foam formation remains below 44° C. or below 51° C. In the range of 44° C. to 51° C., the time to cause thermal injury roughly doubles for every degree. A temperature of 44° C. corresponds to 6 hour to cause injury; therefore the time to cause injury at 49° C. is least 12 minutes, and the cast remains near its peak temperature for about 3 minutes. In some embodiments, the temperature can be controlled by the amount of foam injected, the amount of water blowing agent in the foam precursors, and the composition of the foam precursors. In some embodiments, the foam exerts a pressure on the arm during formation and expansion. In some embodiments, the pressure is minimized to avoid constriction of blood flow. As shown in FIG. 5B, during formation of an exemplary polyurethane foam in a limb stabilization device, the pressure remains below 20 mmHg, below the typical pressures for application of a plaster or fiberglass cast. In some embodiments, the pressure during foam formation remains below 30 mmHg. In some embodiments, the limb stabilization device includes buckles with straps, a zipper, or a ratcheting fastening device to control pressure. In some embodiments, the pressure is controlled by selecting the precursors or the volume of the precursors.

In some embodiments, shown in FIG. 6A-6C, the foam precursors are stored in squeezable pouches 620 prior to delivery. In some embodiment, the squeezable pouches 620 are located within the pouch. In some embodiments, the squeezable pouches are located exterior to the pouch. In some embodiments, the squeezable pouch 620 includes unbreakable seals 621 at the perimeter of the squeezable pouch 620 and breakable seals separating the squeezable pouch 620 from the pouch. In these embodiments, foam precursors are released when the breakable seal is broken. FIG. 6A shows fabrication of a squeezable pouch 620 with two compartments 623a, 623b separated by a breakable seal 622a, according to some embodiments. A first precursor component 606a is added to the first compartment 623a, and a second precursor component 606b is added to the second compartment 623b. As shown in FIG. 6B, the first precursor component A 606a is stored in the first compartment 623a, the second precursor component B 606b is stored in the second compartment 623b, and these precursors are separated by a breakable seal 622a. In some embodiments, the squeezable pouches 620 include a breakable seal 622b separating the squeezable pouches from the rest of the pouch, including, for example, the network of channels. As shown in FIG. 6C, when the breakable seals 622a, 622b are broken, the precursors 606a, 606b mix to form a foam within the squeezable pouch 620 and are able to enter the rest of the pouch, for example for distribution via the network of channels. In some embodiments, the limb stabilization device includes a plurality of squeezable pouches at different locations within or external to the pouch. In some embodiments, the plurality of squeezable pouches contribute to distribution of foam precursors throughout the pouch.

Figure 7B:
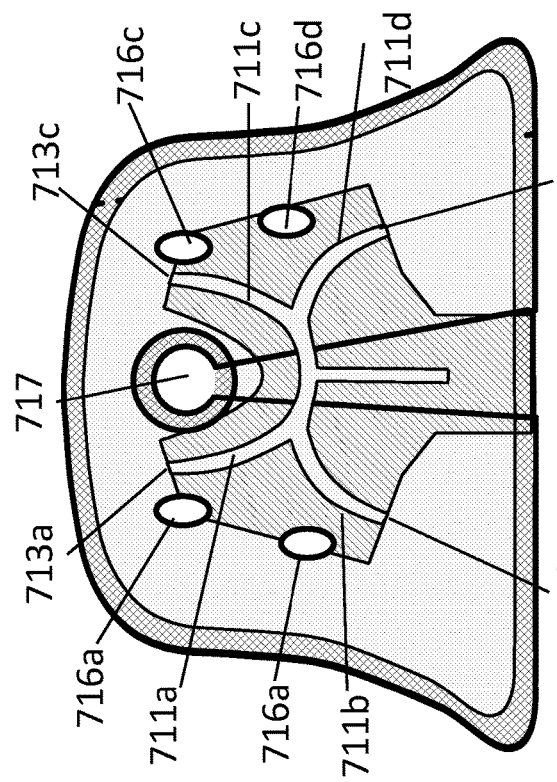
FIG. 7B shows a pouch and sleeve with ventilation holes, according to certain embodiments.
Figure 7A:
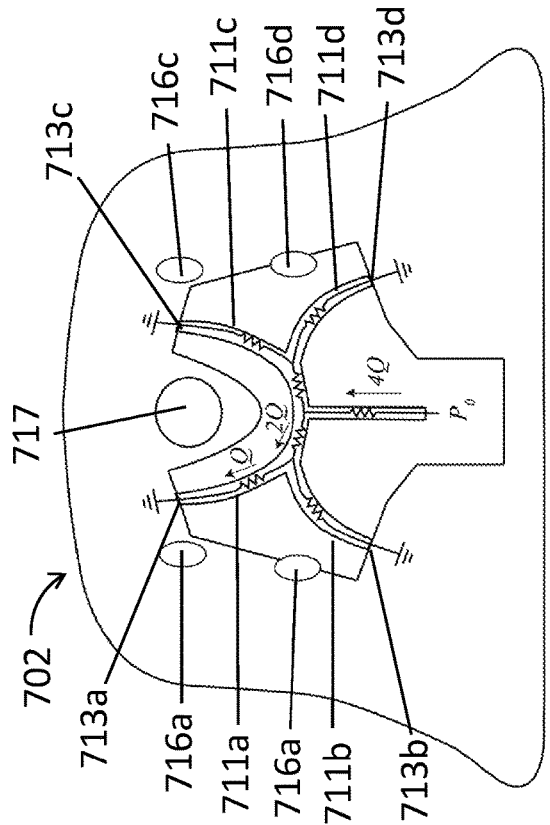
FIG. 7A shows a pouch with ventilation holes, according to certain embodiments.
Figure 7D:
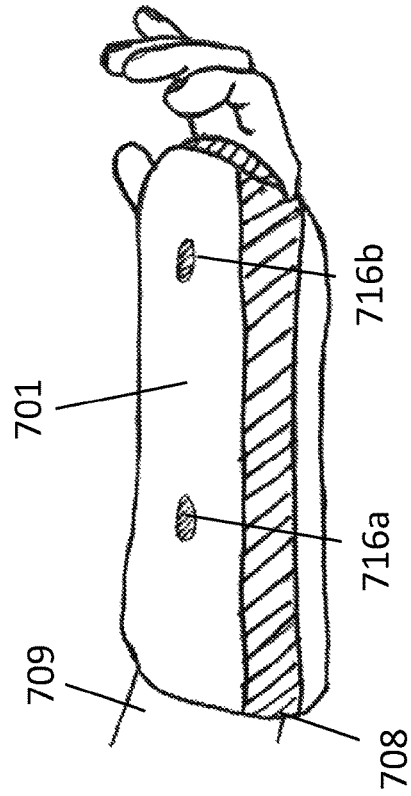
FIG. 7D shows an expanding foam-fabric orthopedic limb stabilization device with ventilation holes, according to certain embodiments.
Figure 7C:
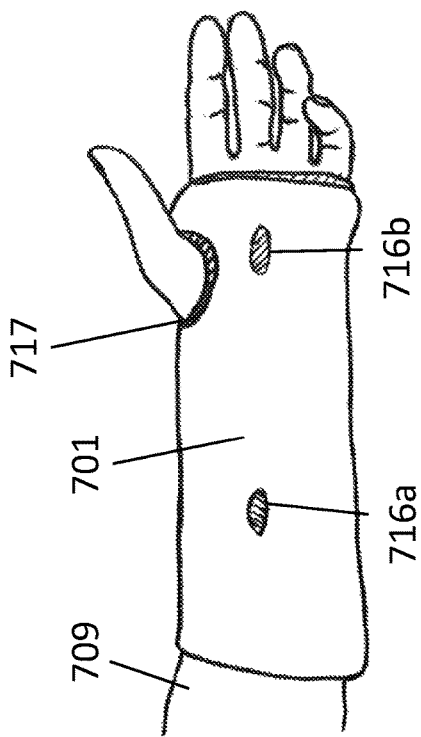
FIG. 7C shows an expanding foam-fabric orthopedic limb stabilization device with ventilation holes, according to certain embodiments.

In some embodiments, shown in FIGS. 7A-7D, the limb stabilization device includes ventilation holes 716a, 716b,

716c, 716d for comfort and circulation of air during wear. FIG. 7A shows ventilations holes in a pouch, while FIG. 7B shows ventilations holes in a pouch overlaid with a sleeve. FIGS. 7C-7D show a limb stabilization device with ventilation holes 716a, 716b on a limb 709. In some embodiments, the limb stabilization device includes ventilation holes in the pouch 702 and in the interior 703 and outer linings 704 of the sleeve 701. In some embodiments, the ventilation holes in the pouch are sealed at the perimeter of the ventilation holes. In some embodiments, ventilation holes are located at the center of the sleeve, for example in regions further from the edges, thumb holes 717, or other areas that already have ventilation. In some embodiments, shown in FIG. 7D, the ventilation holes are located further from the overlapping panel 708. In some embodiments, shown in FIGS. 7A-7B, the ventilation holes are not located near the outlets 713a, 713b, 713c, 713d of the channels 711a, 711b, 711c, 711d to avoid interference with distribution of foam. In some embodiments, the ventilation holes are located directly in front of the outlets or are positioned in a manner that the ventilation holes do not obstruct flow of foam components from the channel outlets.

In some embodiments, the foam can be molded during a limited period of time during foam formation. In some embodiments, the foam precursors are selected to allow sufficient time for molding of the foam in the limb stabilization device. In some embodiments, there are two or more foam precursors, and the relative concentrations of the foam precursors is selected allow sufficient time for molding of the foam. In some embodiments, the foam can be molded for up two to seven minutes. In some embodiments, the foam can be molded for up to two minutes, three minutes, four minutes, five minutes, six minutes, seven minutes, or any time period in between. In some embodiments, the foam expands to its final volume within three to four minutes. In some embodiments, the foam expands to its final volume within three minutes, four minutes, five minutes, six minutes, seven minutes, eight minutes, nine minutes, ten minutes, or any time period in between. In some embodiments, the foam is set and can be handled within about 15-30 minutes. In some embodiments, the foam is set within 15 minutes, 20 minutes, 25 minutes, 30 minutes, or any time period in between. In some embodiments, the foam is fully cured within 2 hours. In some embodiments, the initial molecular weight of the diisocyanate and polyol-based pre-polymers are increased or decreased to either increase or decrease the window of time in which the foam is moldable. For example, higher molecular weight pre-polymers have slower reaction kinetics and take longer to form a fully cured foam.

In some embodiments, the foam is a rigid polymer foam. In some embodiments, the foam has a cellular structure. In some embodiments, foam is lightweight, for example, with a density between about 0.04 g/cm$^3$ and 0.08 g/cm$^3$. In some embodiments, the density is 0.04 g/cm$^3$, 0.05 g/cm$^3$, 0.06 g/cm$^3$, 0.07 g/cm$^3$, 0.08 g/cm$^3$, or any value in between. In some embodiments, the foam has an expansion factor of about 5× to 20× to ensure a conformal fit to the limb. In some embodiments the foam has an expansion factor of 5×, 10×, 15×, 20×, or any value in between. In some embodiments, the foam is radiolucent. For example, in the radiographs show in FIGS. 3A-3C, and the x-ray computed tomography images shown in FIGS. 3C-3D, the foam is radiolucent such that it is possible to monitor healing of a fractured limb. Non-limiting examples of foams include polyurethane and epoxy-based foams. Non-limiting examples of polyurethane foams include diphenyl diisocyanate-based polyurethane.

In some embodiments, the stiffness of the foam is tuned based on density. In some embodiments, the density is controlled by the amount of water mixed in with the precursors. For example, when the foam precursors are polyols, a higher water content leads to a lower density with typical water contents ranging from 0 to 3 parts per hundred of polyols by weight. In some embodiments, the stiffness of the foam is between that of plaster and fiberglass. In some embodiments, the stiffness of the foam is between about 1-100 MPa. In some embodiments, the stiffness is 1 MPa, 2 MPa, 3 MPa, 4 MPa, 5 MPa, 10 MPa, 15 MPa, 20 MPa, 25 MPa, 30 MPa, 35 MPa, 40 MPa, 45 MPa, 50 MPa, 60 MPa, 70 MPa, 80 MPa, 90 MPa, 100 MPa, or any value in between.

Methods

In some embodiments, shown in FIGS. 8A-8G, fabrication of an expanding foam-fabric orthopedic limb stabilization device includes assembling a plurality of layers, each layer cut into an appropriate pattern. In some embodiments, a knit textile is cut into the pattern shown in FIG. 8A for the outer lining 804 of the sleeve. In some embodiments, two polymer sheets 807a are cut into the pattern shown in FIG. 8B to form a pouch. In some embodiments, two cover sheets 818a are cut into the pattern shown in FIG. 8C for fabrication of the pouch. In some embodiments, a knit textile is cut into the pattern shown in FIG. 8D for the inner lining 803 of a sleeve. In some embodiments, a polymer sheet 807b is cut into the pattern shown in FIG. 8E for fabrication of channels in a pouch. FIG. 8F shows a cover sheet 818b for fabrication of channels in a pouch. In some embodiments, a band 808 is cut into the pattern shown in FIG. 8G shows for an overlapping panel of a sleeve.

In some embodiments, shown in FIGS. 9A-9C and FIGS. 10A-10L, fabrication of the sleeve includes of (i) cutting the outer lining and the inner lining into the cast pattern, and (ii) performing a series of sewing and inversion steps. In some embodiments, the sleeve is inverted to attach an overlapping fabric panel and to finish sleeve edges. Although inversions are additional steps, inversions do not necessitate additional seams. In some embodiments, the fabric panel is approximately 1 cm wide and overlaps the sleeve on one side of the limb allow for removal with scissors rather than an oscillatory saw. In some embodiments, the steps in the fabrication process are translatable to manufacturing processes from the garment industry.

In some embodiments, to fabricate a limb stabilization device for a wrist, the outer lining, inner lining, and band are cut into the patterns shown in FIGS. 8A, 8D, and 8G. Then, as shown in FIGS. 9A-9B, the fabric band 908 is sewn to the outer lining 804 at the location indicated by the dotted line. This step is also shown in FIG. 10A. As shown in FIGS. 9C and 10B, the inner lining is then sewn onto the outer lining around the thumbhole 1017 to form seam 1 (1021). If the outer lining 1004 is a laminate, the inner lining is sewn onto the knit side of the outer lining 1004. Then, as shown in FIG. 10C, the ends of the outer lining 1004 and inner lining 1003 are sewn together, forming seam 2 (1022) and seam 3. Then, as shown in FIG. 10D, the sleeve 1001 is inverted a first time by inserting the inner lining 1003 through the thumbhole 1017. FIG. 10E shows the sleeve 1001 after the inversion step. Then, as shown in FIG. 10F, the pouch 1002 is inserted. Then, as shown in FIG. 10G, the first side of the outer lining 1004 is sewn to the inner lining 1003, forming seam 4 (1023), by folding the sleeve over the side. In some embodiments, seam 4 is on the same side as the band. Then, as shown in FIG. 10H, the sleeve is inverted a second time. FIG. 10I shows the sleeve after the second inversion step.

Then, as shown in FIG. 10J, the second side of the outer lining 1004 is sewn to the inner lining by folding the sleeve over the other side, forming seam 5 (1024). In some embodiments, a hole is poked in the outer lining to attach an inlet to the channels of the pouch. Then, as shown in FIG. 10J, the bottom part of the cast is sewn, forming seam 6 (1025) and seam 7, leaving a small hole for the third inversion. In some embodiments, the inner lining is stretched when seams 6 and 7 are sewn. Finally, as shown in FIG. 10K, the sleeve is inverted for a third time. FIG. 10L shows a complete sleeve after the third inversion. This process can be modified to fabrication limb stabilization devices for other parts of the body.

In some embodiments, a stretchable inner knit inner lining pattern is smaller than the outer lining pattern and is pre-strained during the sewing process to mitigate the formation of wrinkles upon expansion of foam, as shown in FIG. 3D. If wrinkling is caused by imperfect molding or uneven overlap in casting tape or padding, there is an uneven distribution of contact pressure between the cast and the skin, leading to subsequent dermal irritation and/or pressure sores. In some embodiments, pre-straining of the inner lining allows the sleeve to stretch into conformal contact with the limb as the foam expands. In some embodiments, pre-straining the inner lining, combined with an expanding foam, also permits sleeves of a few sizes (e.g. small, medium, and large) to support a range of patients while providing a custom fit.

In some embodiments, shown in FIGS. 11A-11C, the pouch is formed by bonding polymer sheets, for example by heat bonding thermoplastic sheets. In some embodiments, the pouch can be formed by heat bonding at 90-200° C. In some embodiments, the polymer sheets are capable of being heat bonded at 90° C., 100° C., 110° C., 120° C., 130° C., 140° C., 150° C., 160° C., 170° C., 180° C., 190° C., 200° C., or an temperature in between. In some embodiments, the heat bonding temperature and time are optimized empirically for the polymer sheet material. In some embodiments, the sheets are heat bonded by applying a pressure of about 100 to 1000 kPa. In some embodiments, the sheets are heat bonded at a pressure of about 100 kPa, 200 kPa, 300 kPa, 400 kPa, 500 kPa, 600 kPa, 700 kPa, 800 kPa, 900 kPa, 1000 kPa, or any value in between. In some embodiments, the sheets are heat bonded for times of about 45-175 seconds. In some embodiments, the sheets are heat bonded for a time of about 45 s, 60 s, 75 s, 90 s, 105 s, 120 s, 135 s, 150 s, 175 s, or any value in between. In some embodiments, a heat-sealing process includes (i) cutting two sheets of thermoplastic polymer into the pattern shown in FIG. 8B, (ii) cutting a spacer sheet (e.g., a sheet of parchment paper) into the pattern shown in FIG. 8C with a negative offset, providing a barrier to heat-sealing and creating a pouch sealed at the edges, and (iii) inverting the pouch prior to sealing the final heat-seam. In some embodiments, the pouch may be sealed at additional locations, for example to form thumbholes in a wrist stabilization device or to form ventilation holes. In some embodiments, inverting the pouch prior to sealing the final heat-seam provides additional area for the expansion of foam around the thumb. In some embodiments, the polymer sheets are heat bonded using a heat press. In some embodiments, a heat press includes a soft polymer foam covered by a Teflon sheet onto which the polymer sheet is place and arranged in a laminated pattern with parchment paper, before covering the polymer sheet with another sheet of Teflon and then pushing a heated plate down over the entire assembly. In other embodiments, polymer sheets could also be bonded with an infrared laser, by machining metal stencils that can selectively bond certain areas of the film, using radiofrequency welding. In these embodiments, a spacer sheet such as parchment paper would not be used.

In some embodiments, channels are formed by heat bonding a polymer sheet to one of the polymer sheets of the pouch. In some embodiments, shown in FIGS. 11A-11C, forming channels using a heat-sealing process includes (i) cutting two sheets of polymer into a the pattern shown in FIG. 11B (ii) cutting spacer sheet into the shape of the channel network shown in FIG. 8F, providing a barrier to heat-sealing thus creating channels, (iii) cutting parchment paper into the pattern shown in FIG. 8C with a negative offset, providing a barrier to heat-sealing and creating a pouch sealed at the edges, and (iv) inverting the pouch prior to sealing the final heat-seam.

In some embodiments, a pouch with channels is formed according to the following process, shown in FIGS. 11A-11C. First, as shown in FIG. 11A, a first thermoplastic sheet 1107a (in the pattern shown in FIG. 8B) is heat pressed or heat bonded to the outer lining 1104, using a cover sheet (shown in FIG. 8C) to pattern a heat seal 1121a around the perimeter of the thermoplastic sheet 1107a. Next, a second thermoplastic sheet 1107b (in the pattern shown in FIG. 8E) is heat pressed onto the first thermoplastic sheet 1107a, using a cover sheet (shown in FIG. 8F) to pattern where a second heat seal 1121b is made to form the channel network 1110. Next, a third thermoplastic sheet 1107c (in the pattern shown in FIG. 8B) is heat pressed to first thermoplastic sheet 1107a, using a cover sheet (shown in FIG. 8C) to pattern a heat seal around the perimeter of the thermoplastic sheets 1107a, 1107c, leaving a space to remove the cover sheet. Finally, as shown in FIG. 11C, the cover sheet is removed, and the bottom of the pouch 1102 is heat sealed 1121c to seal it. In some embodiments, a hole is created at the inlet 1112 of the channel network to insert a tube. In some embodiments, the tubing is sealed with putty sealant tape.

In some embodiments, to apply the limb stabilization device, foam precursors are delivered to the pouch and distributed throughout the pouch. The foam expands within the pouch, conforming to the shape of the limb. In some embodiments, the foam can be molded within about 2 minutes of application.

In some embodiments, shown in FIGS. 4A-4E, foam precursors are distributed throughout the pouch 402 via a network of channels 411a, 411b, 411c, 411d. In these embodiments, the precursors are delivered to the pouch by an inlet 412 and distributed by the channels throughout the pouch 402. In some embodiments, shown in FIGS. 4D-4E, the channels 411a, 411b are oriented downwards so that gravity contributes to distribution of the foam.

In some embodiments, shown in FIGS. 12A-12N, the fabrication process is modified to allow formation of ventilation holes 1216. FIG. 12A shows one side of a sleeve with the pouch 1202 heat bonded to the outer lining 1204 of the sleeve 1201. In some embodiments, both the sleeve 1201 and the pouch 1202 have ventilation holes 1216 and the pouch 1202 is heat bonded to the inner lining 1203 at the perimeter of the ventilation holes 1216 and a thumbhole 1217. FIG. 12B shows the opposite side of a sleeve 1201 with ventilation holes 1216. In this view, the outer lining 1204 and fabric band 1208 are visible. First, as shown in FIG. 12C, the inner lining 1203 is overlaid onto the outer lining 1204, and seam 1 (1221) is sewn around the thumbhold 1217. Then, as shown in FIG. 12D, the ends of the outer lining 1204 and inner lining 1203 are sewn together, forming seam 2 (1022) and seam 3. Then, as shown in FIG. 12E, the sleeve 1201 is inverted a first time by inserting the inner lining 1203 through the thumbhole 1217. FIG. 12F shows the sleeve 1201 after the inversion step. Then, as shown in FIG. 12G, the first side of the outer lining 1204 is sewn to the inner lining 1203, forming seam 4 (1223), by folding the sleeve over the side. In some embodiments, seam 4 is on the same side as the band. Then, as shown in FIG. 12H, the sleeve is inverted a second time. FIG. 12H shows the ventilation holes 1216 in the pouch 1202. FIG. 12I shows the sleeve after the second inversion step. Then, as shown in FIG. 12J, the second side of the outer lining 1204 is sewn to the interior lining by folding the sleeve over the other side, forming seam 5 (1224). Then, as shown in FIG. 12K, the bottom part of the cast is sewn, forming seam 6 (1225) and seam 7, leaving a small hole for the third inversion. Finally, as shown in FIGS. 12L-M, the sleeve is inverted for a third time. FIG. 12M shows a complete sleeve after the third inversion.

Figure 13:
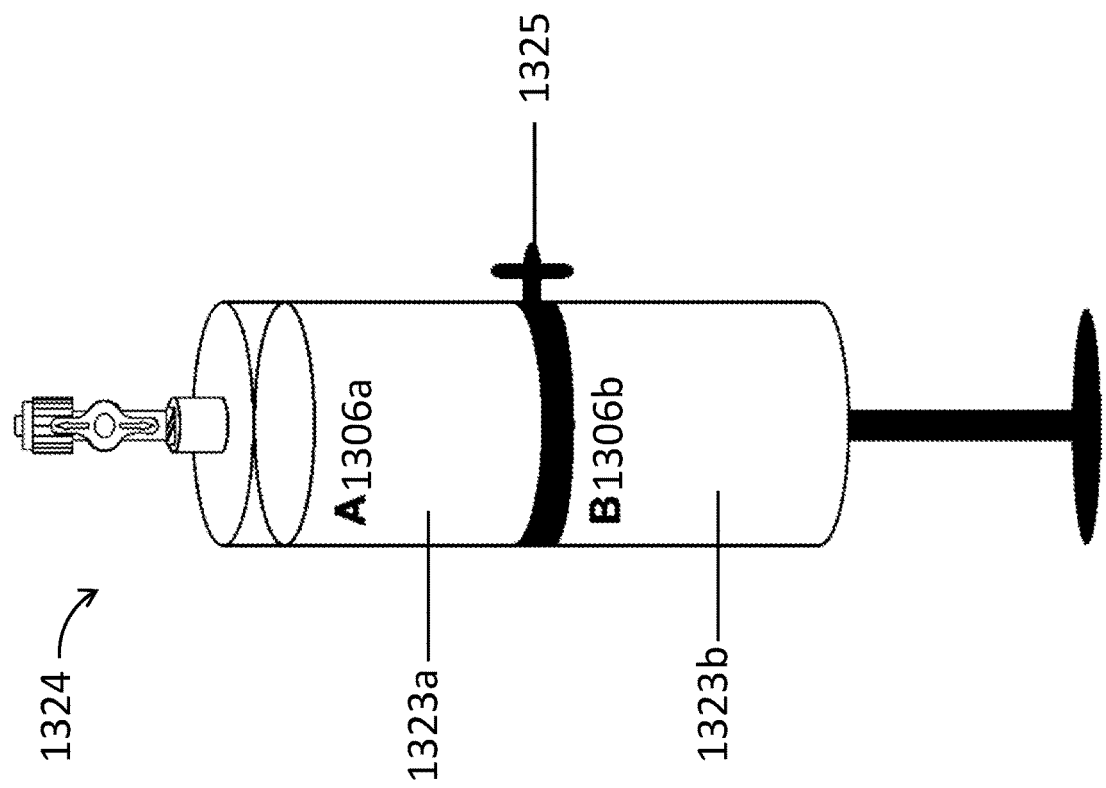
FIG. 13 shows a syringe for delivery of a foam precursor component A and a foam precursor component B, according to certain embodiments.

In some embodiments, the foam precursors are delivered to the pouch via an inlet. In some embodiments, shown in FIG. 13, foam precursors are injected into the pouch using a syringe 1324. In some embodiments, the syringe 1324 includes two compartments 1323*a*, 1323*b* separated by a valve 1325, each compartment containing a foam precursor 1306*a*, 1306*b*. When the valve 1325 is opened, the foam precursors 1306*a*, 1306*b* mix as they are injected into the pouch.

In some embodiments, shown in FIGS. 6A-6B, foam precursors are delivered to the pouch via a squeezable pouch 620. FIG. 6A shows fabrication of a squeezable pouch 620 with two compartments 623*a*, 623*b*, according to some embodiments. In these embodiments, a portion of the perimeter of the squeezable pouch 620 is heat bonded to form an unbreakable seal 621. In these embodiments, a breakable seal 622*a* is formed by heat bonding to create compartments 623*a*, 623*b*. Then, foam precursor component A 606*a* is added to the first component 823*a* and foam precursor B 606*b* is added to the second component 623*b*. As shown in FIG. 6B, the perimeter of the pouch is heat bonded to form an unbreakable seal 621, except for a portion where a breakable seal 622*b* is formed to separate the squeezable pouch 620 from the rest of the pouch. As shown in FIG. 8C, when the breakable seal 622*a* is broken the precursors 606*a*, 606*b* mix within the squeezable pouch. As shown in FIG. 6C, when the breakable seal 622*b* is broken, the precursors 606*a*, 606*b* can enter the rest of the pouch and become distributed to the rest of the pouch, for example via a network of channels. Once the foam precursors 606*a*, 606*b* are distributed throughout the pouch, the foam precursors form a foam. In some embodiments, breakable seals are formed by an adhesive (e.g., double-sided tape), while unbreakable seals are formed by heat pressing.

Figures 14A, 14B, 14C:
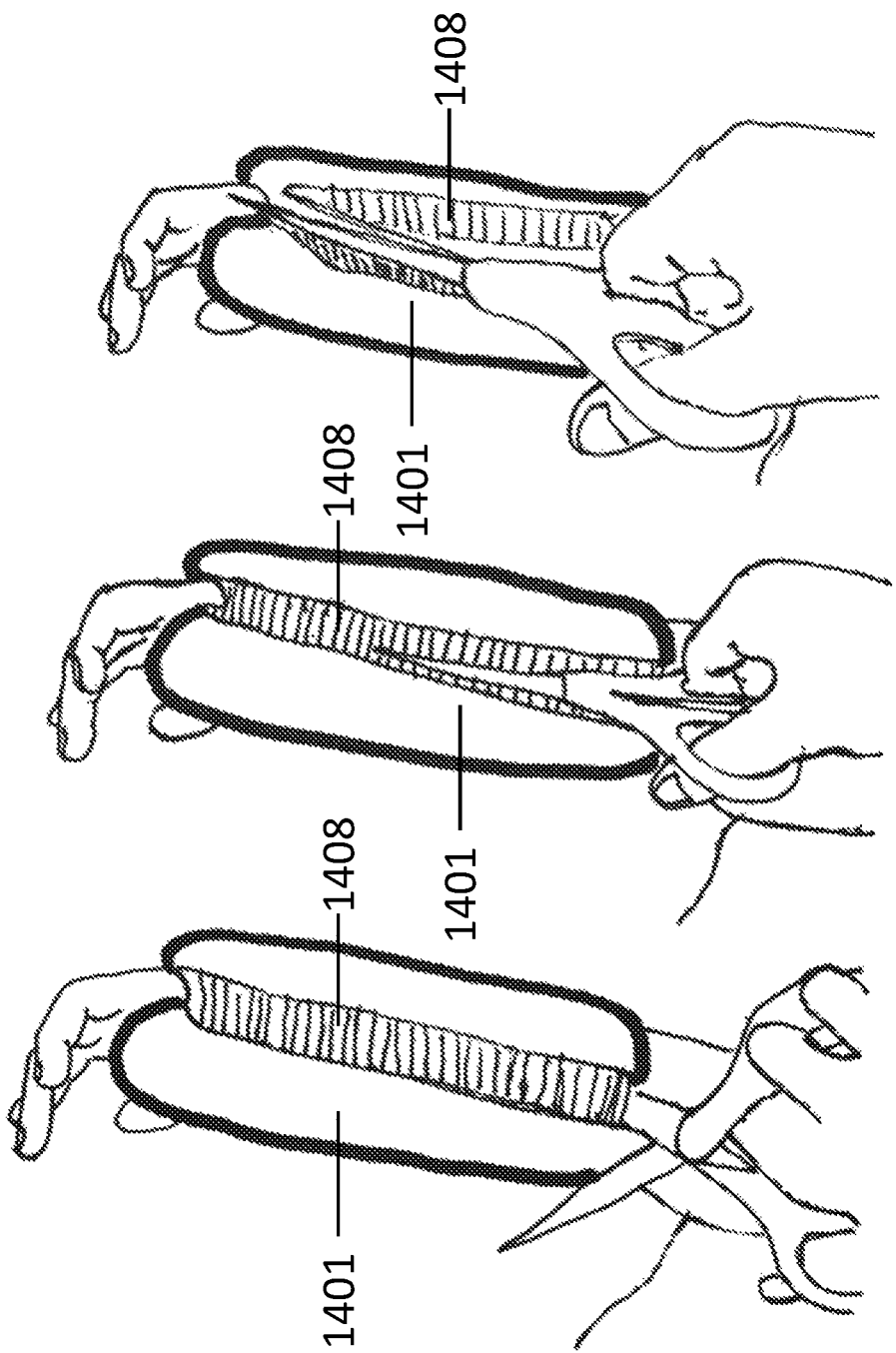
FIG. 14A shows removal of an expanding foam-fabric orthopedic limb stabilization device, according to certain embodiments.
FIG. 14B shows removal of an expanding foam-fabric orthopedic limb stabilization device, according to certain embodiments.
FIG. 14C shows removal of an expanding foam-fabric orthopedic limb stabilization device, according to certain embodiments.

In some embodiments, shown in FIG. 14A-14C, the limb stabilization device can be removed by cutting a fabric panel 1408 of the sleeve 1401. In some embodiments, the sleeve of the limb stabilization device includes an overlapping panel 1408 on one side of the limb. In some embodiments, there is foam in the region of the fabric overlapping panel. In some embodiments, shown in FIG. 14A-14C, this panel can be cut using scissors for simple removal of the limb stabilization device.

Applications

In some embodiments, an expanding foam-fabric orthopedic limb stabilization device can be used to stabilize a limb or other body part after injury. Non-limiting examples of injuries include fractures, sprains, strains, or scoliosis. In some embodiments, the limb stabilization device can be used to stabilize displaced or comminuted fractures. For example, a doctor can set a fractured bone by molding the limb stabilization device while the foam or foam precursors are still moldable. In some embodiments, the limb stabilization device is adapted to conform to parts of the body including the arm, wrist, ankle, leg, foot, fingers, back and neck.

Figures 15A, 15B, 15C:
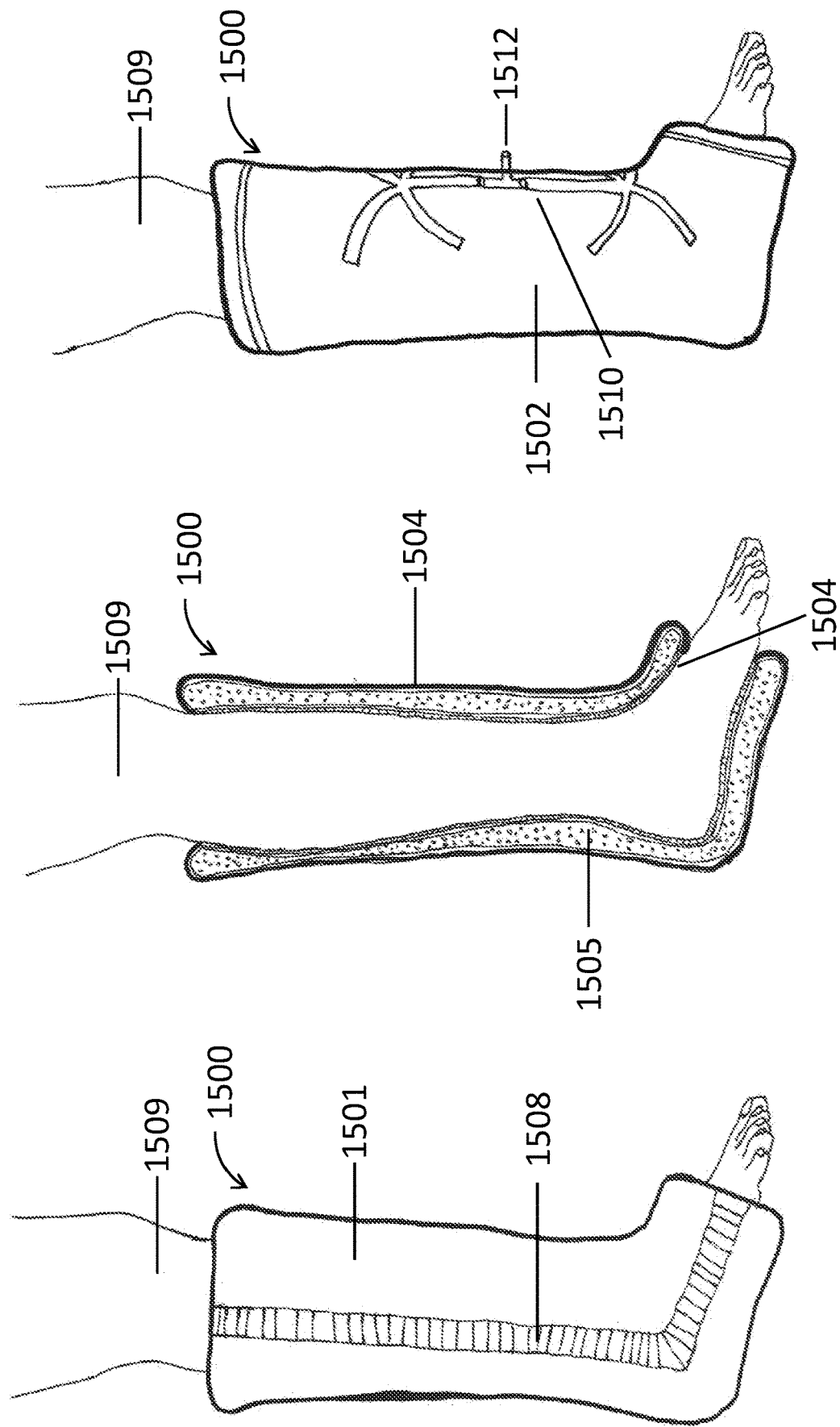
FIG. 15A shows an expanding foam-fabric orthopedic limb stabilization device for a leg or ankle, according to certain embodiments.
FIG. 15B shows a cross-section of an expanding foam-fabric orthopedic limb stabilization device for a leg or ankle, according to certain embodiments.
FIG. 15C shows a pouch of an expanding foam-fabric orthopedic limb stabilization device for a leg or ankle, according to certain embodiments.

For example, as shown in FIGS. 15A-15B, an expanding foam-fabric orthopedic limb stabilization device 1500 can be used to stabilize an ankle or leg 1509. FIG. 15A shows a sleeve 1501 of the limb stabilization device 1500 with a panel 1508 for removal. FIG. 15B shows a cross-section of the limb stabilization device 1500, showing the interior 1503 and exterior 1504 layers of the sleeve and the foam 1505 within the pouch. FIG. 15C shows the pouch 1502, with a channel network 1510 and inlet 1512 for distribution of foam precursors.

Figure 16:
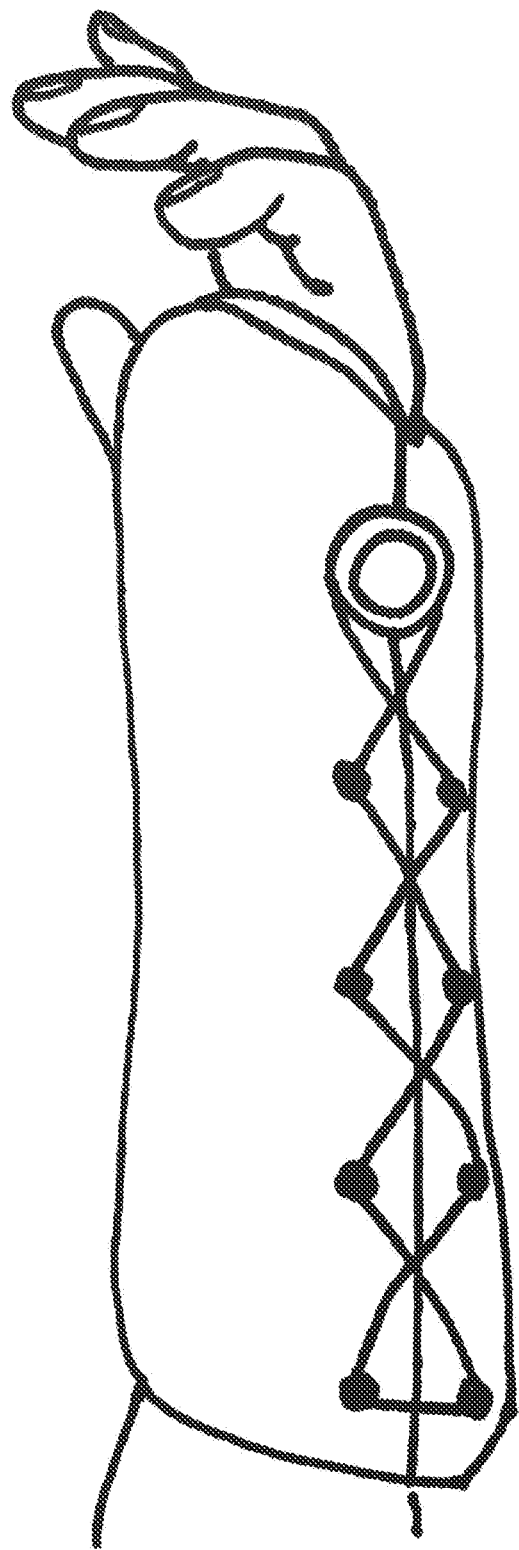
FIG. 16 shows a ratcheting fastening device to control pressure, according to certain embodiments.

In some embodiments, the stabilization device is a back brace for treatment of scoliosis. In some embodiments, the stabilization device surrounds the torso and an arm for treatment of brachial plexus palsy. In this application, the stabilization device will function to hold the arm at 90 degrees of abduction from the body under a maximum external rotation. In some embodiments, the stabilization device is shaped like a sock and can fit on a patient wearing a shoe. In some embodiments, the limb stabilization can be deployed in the field without an orthopedic surgeon, for example when hiking, in combat, in emergency medicine situations, or in low-resource areas. In some embodiments, shown in FIG. 16, the limb stabilization device includes a ratcheting fastening device to control pressure. Such a ratcheting fastening device allows for the adjustment of pressure through the application of tension to laces holding the cast together by turning a ratcheting spool. When the pressure needs to be released, e.g., for cast removal, the ratchet is disengaged and the tension is released.

EXAMPLES

Certain embodiments will now be described in the following non-limiting examples.

Polyurethane Foam

A rigid polymer foam was used as the structural component for the limb stabilization device based on two considerations. First, when the foaming reaction is initiated, the liquid undergoes a simultaneous expansion and solidification process, such that the foam molds to the shape of the object that constrains its expansion (i.e. a foam-in-place process). Second, the cellular structure makes the foam lightweight while retaining mechanical strength. A commercially available, two-component, methylene diphenyl diisocyanate-based polyurethane (PU) closed-cell foam was used. This foam had the following characteristics: (i) the reacting liquid expands to its full volume in 4 minutes, can be handled after 20 minutes, and is fully cured in 2 hours (ii) the foam has an expansion factor of 18×, ensuring a conformal fit to the limb and a low mass density (0.048 g/cm$^3$) and (iii) the foam costs~500 per cast. Moreover, such a formulation can be modified to increase or decrease the density of the foam or the speed of the foaming reaction. Foams of increased density were also evaluated, but the low density foam (0.048 g/cm$^3$) was selected after experimentally determining that casts made from this foam exhibited sufficient mechanical strength and required less material—reducing both cost of materials and the weight of the cast.

Fabric Sleeve with Thermoplastic Pouch

A prototype cast was designed for the wrist because fractures of the distal radius are particularly prevalent. The prototype had an exterior fabric sleeve with an interior thermoplastic pouch to contain and guide the foam's expansion.

For the prototype sleeve's outer lining, a commercially available, polyester-thermoplastic polyurethane (TPU) laminate (TS-100B, Eastex Products©) was chosen. This fabric: (i) is comfortable (ii) can be sewn with conventional methods, (iii) has a liquid-resistant exterior and a liquid-proof interior, providing an effective barrier between the skin and foam components, and (iv) is approved for biomedical use and extended dermal contact.

For the prototype sleeve's inner lining, a commercially available, knit spacer fabric (90% Polyester/10% Spandex, Fabric Wholesale Direct) was chosen. This fabric's role was to promote patient comfort by preventing the formation of wrinkles on the cast's interior and subsequent pressure sores and/or dermal irritation. The knit spacer fabric's tensile properties allowed creation of a cast with an inner portion sized significantly smaller than the outer portion of the cast, placing unidirectional strain on the sleeve's inner lining for a precise fit.

The fabrication process of the sleeve included (i) cutting a thermoplastic polyurethane (TPU) elastomer-coated polyester knit (outer lining) and a stretchable knit spacer fabric (inner lining) into the cast pattern, and (ii) performing a series of sewing and inversion steps. Sewing was completed with a lockstitch to prevent the seam from stretching, thus maintaining the sleeve shape and durability, and allowing for efficient and easily implementable manufacturing. Each seam was sewn on the TPU-coated interior of the sleeve to promote patient comfort. The sleeve was inverted to attach an overlapping fabric panel and to finish sleeve edges. Although inversions are additional steps, they do not necessitate additional seams. The sleeve included fabric panel approximately 1 cm wide and that overlapped the cast on the ulnar side of the patient's wrist to allow for removal with scissors rather than an oscillatory saw. This overlap ensured circumferential cast coverage: there still existed foam protection of the fractured bone beneath this band. All the steps in the fabrication process are translatable to manufacturing processes from the garment industry.

The stretchable inner knit spacer fabric pattern is smaller than the outer polyester-TPU fabric pattern and is pre-strained during the sewing process to mitigate the formation of wrinkles upon expansion. Wrinkling—caused by imperfect molding or uneven overlap in casting tape or padding—leads to an uneven distribution of contact pressure between the cast and the skin, and subsequent dermal irritation and/or pressure sores. The pre-straining of the inner lining allowed the garment to stretch into conformal contact with the skin as the foam expands. This strategy, in combination with the PU foam properties previously mentioned, also permits garments sized S, M, and L to support a range of patients while providing a custom fit. In accordance with existing guidelines for short-arm casts, the fabric garment was designed to extend from the distal palmar crease to the proximal third of the forearm.

The interior pouch included a thermoplastic film. For the pouch, a commercially available, Stretchlon® 200 Bagging Film was chosen. This material is fluid-proof (providing an extra layer of patient protection against dermal contact with the foam) and can be purchased for $.53 USD per cast. Additionally, this material is heat-sealed in under 45 seconds at a temperature of 140° C. The heat-sealable nature of this material allows for incorporation of fluidic channels for distributing the foaming liquid (foam precursors) directly into the pouch. The pouch provided an extra layer of patient protection against dermal contact with the liquid foam components, assisting in the prevention of allergic contact dermatitis, which has increased in incidence due to the common use of fiberglass synthetic casts and undercast cotton padding with synthetic fibers.

The interior pouch was fabricated through a heat-sealing process. The heat-sealing process, shown in FIGS. 11A-11C involved: (i) cutting two pieces of TPU into the cast pattern (ii) cutting parchment paper into the spider-like channel shape, providing a barrier to heat-sealing thus creating fluidic channels, (iii) cutting parchment paper into the cast-pattern with a negative offset of approximately 1 cm, providing a barrier to heat-sealing and creating a pouch sealed at the thumbhole and edges, and (iv) inverting the pouch prior to sealing the final heat-seam, which provides additional area for the expansion of foam around the thumb.

The pouch also guided foam expansion and acted as a pressure-venting system. Small holes were made with a 16-gauge butterfly needle in the TPU facing outward from the patient's arm. These holes blocked the flow of the viscous foam out of the pouch yet allowed excess air or other gas to escape, preventing the formation of larger air bubbles which otherwise would cause a buildup of pressure and inhibit the uniform distribution of the foam. Fluidic channels were incorporated into the pouch through a patterned heat-sealing process to direct the liquid foam evenly to the four corners of the cast with respect to gravity. Initial estimates for the width of the fluidic channels were determined by specifying the lengths of the branching channels, assuming Hagen-Poiseuille flow and solving for the set of fluidic resistances, $\{R1\text{-}R3\}$ $[N \cdot s/m^5]$ that would yield equivalent flow rates, $Q$ $[m^3/s]$, at each outlet. The channel geometries were subsequently optimized empirically to ensure uniform foam distribution. In an embodiment, the total fluidic resistance of the branched channels is in the range 0.1-2 kPa/cm$^3$, to allow for the facile manual injection of the foam precursors. Optimizations included tapering the channel outlets to decrease the likelihood that the liquid foam would flow out of one channel prior to reaching the ends of the others, as well as curving of the branches.

Cast Application

To apply the cast, the liquid foam precursors were loaded into a 60 mL syringe containing a Luer lock. The syringe was shaken for approximately 30 seconds; sufficient mixing was indicated by a uniform beige color of the mixed components. The liquid was then injected through a valve that is Luer-locked with the cast. The foam traveled through the channels within the TPU pouch and finally expanded, conforming to the shape of the patient's arm over the course of approximately 3 minutes. In these experiments, there was a ~2 min period of time during the expansion process where a gentle pressure to the cast's exterior could be used to mold the foam. Molding was unnecessary for effective application but can be performed if the clinician desires to make adjustments to the shape of the cast. This window of time can be tailored for the specific needs of physicians using formulation chemistry in tandem with time-dependent rheological experiments. The cast is depicted both pre and post-expansion in FIGS. 4B-4E. The cast was set ~5 minutes after the foam was injected and was fully cured in two hours. In comparison, fiberglass casts are able to bear pressure approximately 30 minutes post-application, while plaster can take up to 2 days to fully cure.

Cast Removal

Complications of cast saw use include (1) abrasions or lacerations occurring when the blade comes into contact with the skin or (2) burns caused by the heat from friction between the saw blade and the cast material. As shown in FIGS. 14A-14C, the expanding foam-fabric orthopedic limb stabilization device circumvented this issue with the fabric band overlap, which allowed the cast to be removed with a pair of scissors cutting along the fabric band. Underneath this fabric band existed an overlapping region of polyurethane foam, allowing for easy removal without the compromise of mechanical strength.

Replica Wrist Testing

Testing and iterative development of the prototype were performed on a replica arm constructed from a practice suture arm, into which a 3D-printed skeleton was inserted and held in place by either a flexible foam, as shown in FIG. 3C, or silicone, as shown in FIG. 3D. The use of a replica arm allowed for the characterization of solidified casts prior to removal using radiographs (FIGS. 3A-3B) or X-ray based computed tomography (CT) imaging (FIGS. 3C-3D). CT scans were employed to i) confirm the uniform expansion of the foam (i.e. the absence of macroscopic bubbles of air), ii) and guide the design of the cast interior, using pre-strained fabric to prevent wrinkle formation. As shown in FIG. 3C, when the inner lining of the sleeve was not pre-strained, wrinkles (indicated by asterisks) formed in the inner lining against the skin of the replica arm as the foam expanded. In contrast, as shown in FIG. 3D, when the inner lining was pre-strained, wrinkles did not form in the inner lining as the foam expanded. These experiments also demonstrate the radiolucency of the foam fabric limb stabilization device, an attribute that allows physicians to monitor the progression of bone healing without cast removal.

CT images were acquired with the Nikon X-tek HMXST225 imaging system. X-rays were produced from an x-ray tube containing a tungsten target, operating at a voltage of 85 kV and a current of 115 µA. A total acquisition time of ~110 minutes was employed, with two frames acquired per projection. To enhance the X-ray absorption of the inner lining, the fabric was soaked in an aqueous contrast agent solution containing 3.05% potassium iodide and 1.85% iodine (Innovating Science), then allowed to dry before incorporation into the cast.

Application Temperature

Given the exothermic nature of the foaming reaction, the heat released during application of the expanding foam-fabric orthopedic limb stabilization device should be dissipated effectively to mitigate risk of thermal injury. Dermal temperature was monitored throughout the application process using a thermocouple placed between the patient's forearm and the cast. As shown, in FIG. 5A, the temperature peaked at a value of 43.6° C. approximately 3 minutes after foam injection. The foam was moldable within the first two minutes of application. This temperature is comparable to temperatures experienced during both fiberglass and plaster cast application (fiberglass casts produce internal temperatures of approximately 45° C. and exhibits almost no risk of thermal injury during cast application, while plaster casts can produce internal temperatures>49° C. and exhibit modest risks for thermal injury). This temperature is also below the temperatures at which humans may begin to experience pain (47° C.). Additionally, the application process does not require the use of dipping water. In contrast, fiberglass and plaster cast application temperatures vary significantly, and may reach dangerously high internal temperatures, if the temperature of the dipping water and the amount of water squeezed out of the casting tape are not monitored. It was thus determined that the limb stabilization device does not pose an additional risk of thermal injury during application.

Application Pressure

The pressure applied by an orthopedic cast should be minimized (under≈30 mmHg) to prevent the constriction of blood flow. Casts can exert mean pressures of 31±3 mmHg without occluding the microcirculation of the skin. The pressure, P [mmHg], that builds up within the expanding foam-fabric orthopedic limb stabilization device is due the circumferential strain, ε, induced in the fabric expanded to radius, r [cm], and is determined by the following parameters: the initial volume of the liquid foam, $V_i$ [cm$^3$], the expansion factor of the foam ($\alpha$), the approximate radius of the subject's arm, $r_0$ [cm], the unperturbed radius of the exterior fabric layer, $r_0$ [cm], the length of the cast, L [cm], and the tensile properties of the exterior fabric layer—tensile modulus times thickness, Et [mm Hg·cm]. As shown in FIG. 5B, experiments showed that if the initial volume of the foam was chosen such that only a small amount of tension was produced upon foam expansion, then the pressure would peak below 30 mmHg. The foam was moldable within the first two minutes of application. Moreover, the buildup of pressure can be described by the equation below, derived with the assumptions of cylindrical Laplace pressure, unperturbed expansion of the foam, and linear elasticity of the fabric membrane (ε<0.1):

$$P = \frac{Et\epsilon}{r} = \frac{Et}{r_0} - Et\left(\frac{V_i\alpha}{\pi L} + r_s^2\right)^{-\frac{1}{2}}$$

During human subject testing, pressure can be measured using capacitive pressure sensors based on a conductive fabric and a microporous dielectric layer. Sensors can be placed in six locations between the cast and the arm, including the bony prominences of the wrist and the area surrounding the thumbhole (areas particularly prone to dermal irritation). Preliminary measurements using a pressure mapping sensor and a replica wrist indicated pressure was distributed evenly.

Figure 19:
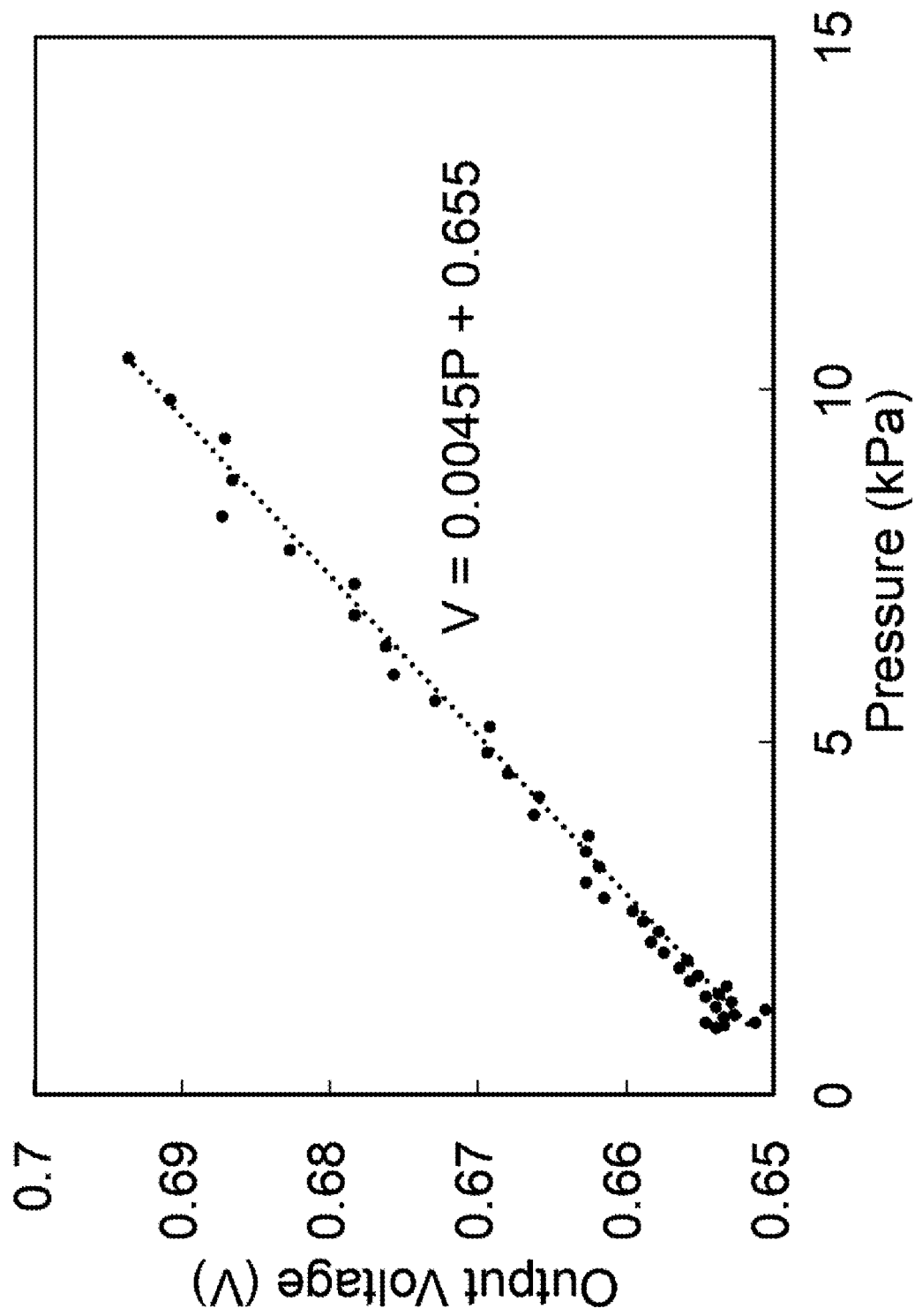
FIG. 19 shows calibration of a capacitive pressure sensitive, according to certain embodiments.

Pressure exerted on a replicate wrist was measured using capacitive pressure sensors. The devices include two layers of a conductive knit textile (Shieldex® Technik-tex P130+B, V Technical Textiles, Inc.) separated by a spacer fabric (90% Polyester/10% Spandex, Fabric Wholesale Direct), which acts as a dielectric layer. The three textile layers were laminated together using a thermoplastic film (3914, Bemis Associates Inc.) and heat-sealed at a temperature of 240° F. for a duration of 30 seconds. The conductive textile layers include excess fabric that cut into opposing channels. These channels allow for connection to a capacitance meter. The capacitance meter converts the force applied on the sensor to an output voltage, which corresponds to an applied pressure. To calibrate the sensors, sensors were indented at a constant rate of strain while monitoring the voltage and pressure to produce the linear calibration curve shown in FIG. 19. A total of 6 sensors were tested, and all produced curves.

Mechanical Testing

Mechanical tests were performed with an Instron testing system series 5560 with dual column tabletop model 5566 and a 10 kN load cell. All experiments were performed at a loading rate of 50 mm/min.

The function of an orthopedic cast is to mechanically stabilize a fractured bone during the healing process. To provide a preliminary evaluation of the efficacy of the expanding foam-fabric orthopedic limb stabilization device under clinically relevant loading conditions, symmetric three-point flexural tests were conducted on hollow cylindrical samples (length 30 cm and inner diameter≈7 cm). As shown in FIG. 17A, during the flexural tests, hollow cylinder samples were stabilized using two 3D printed support stands spaced a distance L apart. Each support stand exerts a force of one half P upward when a load P is applied downward at the center of the cylinder. The displacement δ of the cylinder at the center was measured. A loading rate of 50 mm/min was applied until failure, and failure was defined by substantial buckling of the structure. Direct comparisons of light and dense foams were made to existing casting materials, including fiberglass (3M™ Scotchcast™ Rigid Casting Tape), plaster (BSN Medical GYPSONA Plaster of Paris), and soft fiberglass (3M™ SoftCast®). Hollow cylinders representing plaster, fiberglass, and soft fiberglass were formed by wrapping casting tape around a PVC pipe with a length 31 cm and an outer diameter of 10 cm. Casts were wrapped in accordance with orthopedic and manufacturer recommendations by overlapping the tape by approximately one half the width of the tape. All hollow cylinders were left to fully cure for 5 days prior to testing. The resulting casts were 4 layers thick. Foam hollow cylinder were made to be the same length as fiberglass and plaster casts (31 cm), with material pre-strained by~10%. A thumbhole was excluded from the hollow cylinder to provide a better comparison to the other materials. The initial slope of the load vs. extension curve provided the bending stiffness of the structure. FIG. 17B shows that the bending stiffness of the foam cast can be modified by altering the density of the foam: a cast made from a dense foam (0.08 g/cm$^3$) had a bending stiffness comparable to that of fiberglass and a cast made from a light foam (0.048 g/cm$^3$) had a bending stiffness comparable to a plaster cast. Both the light and dense foam casts tested were stiffer and stronger than the soft fiberglass. As shown in FIG. 17C, the total work at a displacement of 1 cm was calculated to provide a figure-of-merit to compare the relative strengths of the casting materials. The work of displacement was based on indentation of the hollow cylinders and the error bars indicate 95% confidence intervals of the mean. The work of displacement is a measure of the resilience of the structure, indicating the ability of the structure to absorb energy elastically upon loading, and release energy upon unloading. FIGS. 17D-17G show the displacement of each hollow cylinder foam under three point bending. FIG. 17D shows light foam, FIG. 17E shows fiberglass, FIG. 17F shows plaster, and FIG. 17G shows soft fiberglass. These experiments and analyses show that the mechanical properties of the foam cast can be tuned to either improve upon or provide substantially equivalent mechanical reinforcement to fiberglass and plaster casts.

Figure 18C:
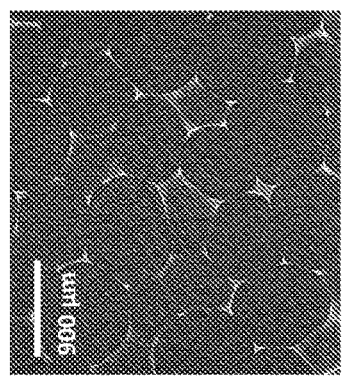
FIG. 18C shows a transverse cross-section of a computed tomography image of a foam cylinder before compression, according to certain embodiments.
Figure 18E:
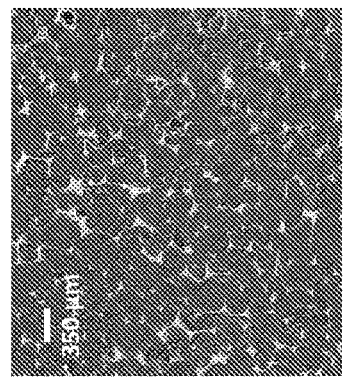
FIG. 18E shows a transverse cross-section of a computed tomography image of a foam cylinder after compression, according to certain embodiments.
Figure 18B:
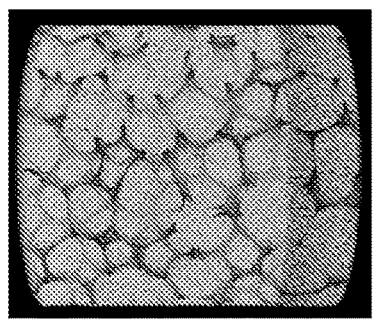
FIG. 18B shows a three-dimensional computed tomography image of a foam cylinder before compression, according to certain embodiments.
Figure 18D:
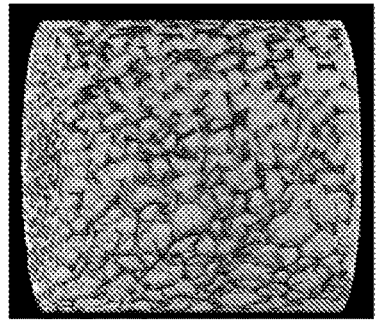
FIG. 18D shows a three-dimensional computed tomography image of a foam cylinder after compression, according to certain embodiments.
Figure 18A:
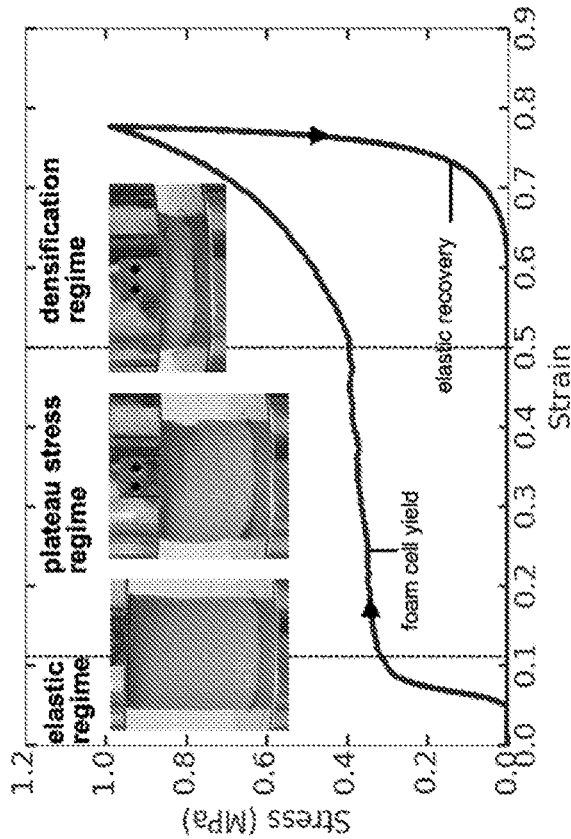
FIG. 18A shows a stress-strain curve with deformation regimes of a foam cylinder loaded in compression, according to certain embodiments.

Cylinders of foam were tested in compression. FIG. 18A shows compressive stress vs. compressive strain plot for a cylindrical slab of polyurethane foam with radius~3.8 cm and density 0.048 g/cm$^3$. Inset photos depict foam slabs under various levels of compression corresponding to the three regimes of foam mechanics: elastic regime, plateau stress regime (including foam cell yield), and densification regime (including partial elastic recovery). FIGS. 18B and 18C show computed tomography images of a foam cylinder before compression. FIGS. 18D-18E show computed tomography images of a foam cylinder after compression and a partial elastic recovery. As seen in FIGS. 18D-18E, compression results in densification of the foam.

Squeezable Pouch

FIGS. 6A-6B show a user-friendly application mode, including of a thermoplastic pouch containing a breakable seal that initially separates two foam precursor components. When the cast is being applied, the seal is manually broken and the two fluids are mixed for 45 seconds. Following mixing, the reactive liquid is pushed into the branched channels of the other thermoplastic pouch to distribute the foam around the wrist.

Scanning Electron Microscope

The sleeve outer lining, sleeve inner lining, and foam were observed using a scanning electron microscope (SEM). SEM images were acquired with a Zeiss FESEM Ultra Plus with an operating voltage of 10 kV and a magnification of 74×. The non-conductive samples were sputter-coated with a thin film of platinum prior to imaging to prevent excess surface charging on the sample. FIGS. 1E-1G show SEM images of exemplary components of an expanding foam-fabric orthopedic limb stabilization device. FIG. 1E shows an SEM image of an outer lining made of a polyester-thermoplastic polyurethane laminate. FIG. 1F shows an SEM image of an inner lining made of a knit spacer fabric, showing the 3-dimensional structure containing voids that allow for breathability and compressibility of the fabric layer. FIG. 1G shows an SEM image of an closed-cell polyurethane foam.

It will be appreciated that while one or more particular materials or steps have been shown and described for purposes of explanation, the materials or steps may be varied in certain respects, or materials or steps may be combined, while still obtaining the desired outcome. Additionally, modifications to the disclosed embodiment and the invention as claimed are possible and within the scope of this disclosed invention.

The invention claimed is:

1. A kit comprising
   a sleeve comprising an outer lining and an inner lining;
   a pouch arranged within the sleeve and comprising one or more polymer sheets, a plurality of channels, and a plurality of vents; and
   a foam precursor capable of forming a foam within the pouch;
   wherein the plurality of channels have a common inlet, and each of the plurality of channels each comprises an outlet.

2. The kit of claim 1, wherein the foam precursor comprises a first component and a second component capable of forming the foam when mixed together.

3. The kit of claim 2, wherein the pouch comprises a first squeezable pouch containing the first component and a second squeezable pouch containing the second component, wherein the first and second squeezable pouches are configured to release the first and second components such that the first and second components mix together.

4. The kit of claim 1, wherein the outer lining comprises a knit textile, a woven textile, a stretchable woven textile, a nonwoven textile, or combinations thereof.

5. The kit of claim 1, wherein the outer lining comprises a laminate sheet comprising a polymer layer and a textile selected from the group consisting of a knit textile, a woven textile, a stretchable woven textile, a nonwoven textile, and combinations thereof.

6. The kit of claim 1, wherein the outer lining is stiffer than the inner lining.

7. The kit of claim 1, wherein the inner lining comprises a knit spacer fabric or an open-celled, soft polymer foam.

8. The kit of claim 1, wherein the inner lining is pre-strained.

9. The kit of claim 1, wherein the one or more polymer sheets comprise thermoplastic polymers.

10. The kit of claim 1, wherein the total resistance of each of the plurality of channels is equal.

11. The kit of claim 1, wherein the diameter of each of the plurality of channels decreases at the outlet.

12. The kit of claim 1, wherein the each of the plurality of channels are branched at the outlet.

13. The kit of claim 1, wherein the plurality of channels are configured to deliver the foam precursor to each corner of the pouch.

14. The kit of claim 1, wherein the plurality of channels are configured such that the plurality of channels are oriented downwards when the foam precursor is injected.

15. The kit of claim 1, wherein the plurality of vents have a greater density at the center of the pouch.

16. The kit of claim 1, further comprising a plurality of ventilation holes in the pouch and the sleeve.

17. The kit of claim 1, wherein the pouch comprises a squeezable pouch containing the foam precursor, wherein the squeezable pouch is configured to release the foam precursor.

18. A method of stabilizing a body part comprising
providing a sleeve comprising an outer lining and an inner lining around a body part;
providing a pouch arranged within the sleeve and comprising one or more polymer sheets, a plurality of channels, and a plurality of vents;
providing a foam precursor in the pouch; and
forming a foam within the pouch;
wherein the plurality of channels have a common inlet, and each of the plurality of channels each comprises an outlet.

19. A kit comprising
a sleeve comprising an outer lining and an inner lining;
a pouch arranged within the sleeve and comprising one or more polymer sheets, a plurality of channels, and a plurality of vents; and
a foam precursor capable of forming a foam within the pouch;
wherein the plurality of channels are configured to deliver the foam precursor to each corner of the pouch.

* * * * *